United States Patent
Ogawa et al.

(10) Patent No.: US 8,891,845 B2
(45) Date of Patent: Nov. 18, 2014

(54) IMAGE PROCESSING APPARATUS AND IMAGE PROCESSING METHOD

(71) Applicant: Telesystems Co., Ltd., Osaka-shi, Osaka (JP)

(72) Inventors: Koichi Ogawa, Tokyo (JP); Akitoshi Katsumata, Ichinomiya (JP); Tsutomu Yamakawa, Osaka (JP); Hideyuki Nagaoka, Osaka (JP); Tatsuya Nagano, Osaka (JP)

(73) Assignee: Telesystems Co., Ltd.

( * ) Notice: Subject to any disclaimer, the term of this patent is extended or adjusted under 35 U.S.C. 154(b) by 0 days.

(21) Appl. No.: 14/128,717

(22) PCT Filed: Sep. 28, 2012

(86) PCT No.: PCT/JP2012/075159
§ 371 (c)(1),
(2), (4) Date: Dec. 23, 2013

(87) PCT Pub. No.: WO2013/047788
PCT Pub. Date: Apr. 4, 2013

(65) Prior Publication Data
US 2014/0193768 A1     Jul. 10, 2014

(30) Foreign Application Priority Data
Sep. 28, 2011   (JP) ................. 2011-212543

(51) Int. Cl.
 *G06K 9/00* (2006.01)
 *A61B 6/00* (2006.01)
 *A61B 6/14* (2006.01)

(52) U.S. Cl.
 CPC .............. *A61B 6/5241* (2013.01); *A61B 6/463* (2013.01); *A61B 6/14* (2013.01); *A61B 6/469* (2013.01)
 USPC ......................................... 382/128; 382/132

(58) Field of Classification Search
 USPC .................. 382/128, 132, 154; 378/4, 18, 38; 348/36, 42
 See application file for complete search history.

(56) References Cited

U.S. PATENT DOCUMENTS 6,196,715 B1 *  3/2001  Nambu et al. .............. 378/197
6,434,279 B1 *  8/2002  Shiba ........................ 382/294

(Continued)

FOREIGN PATENT DOCUMENTS

| JP | 2007-068554 A | 3/2007 |
| JP | 2009-146178 A | 7/2009 |
| JP | 2009-268641 A | 11/2009 |
| WO | WO-2011-016508 A1 | 2/2011 |

OTHER PUBLICATIONS

Koichi Ito et al., "A Palmprint Recognition Algorithm Using Phase-Only Correlation", MIRU 2006, issued in Jul. 2006.

(Continued)

*Primary Examiner* — Samir Ahmed
(74) *Attorney, Agent, or Firm* — Harness, Dickey & Pierce, PLC

(57) ABSTRACT

A panoramic imaging apparatus functionally includes an image processing apparatus. In this apparatus, two planar images are produced, which are subjected to registration. A registration process is applied to overall areas of two planar images based on curves decided from positions designated on the two planar images respectively. The positions on each of the planar images are aligned along a straight line, both straight lines corresponding to each other in a horizontal direction, and a scale factor for the registration is changed position by position on the straight lines. One of the two planar images is searched for a match of each local region of the other planar image, to any of regions of the one planar image, and images of the matched regions are re-produced to produce a planar image. The difference information is calculated between the planar images.

19 Claims, 23 Drawing Sheets

(56) References Cited

U.S. PATENT DOCUMENTS

| | | | |
|---|---|---|---|
| 6,690,761 B2 * | 2/2004 | Lang et al. | 378/56 |
| 7,379,584 B2 * | 5/2008 | Rubbert et al. | 382/154 |
| 7,720,307 B2 * | 5/2010 | Iizuka | 382/281 |
| 2007/0036410 A1 | 2/2007 | Ida et al. | |
| 2012/0328071 A1 | 12/2012 | Katsumata et al. | |

OTHER PUBLICATIONS

International Search Report for PCT/JP2012/075159, ISA/JP, mailed Nov. 6, 2012.

* cited by examiner

FIG.8
(A)
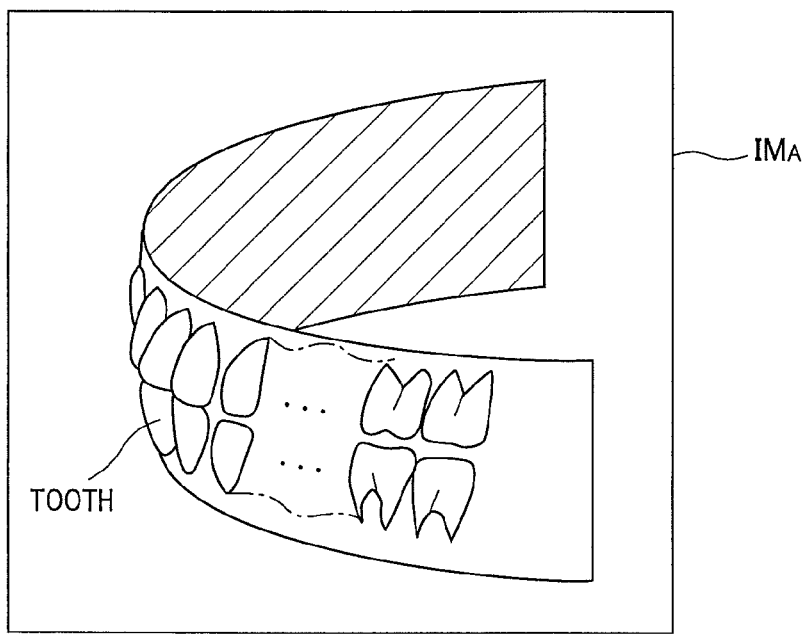
3D AUTOFOCUS IMAGE [ T=T1 ]
(B)
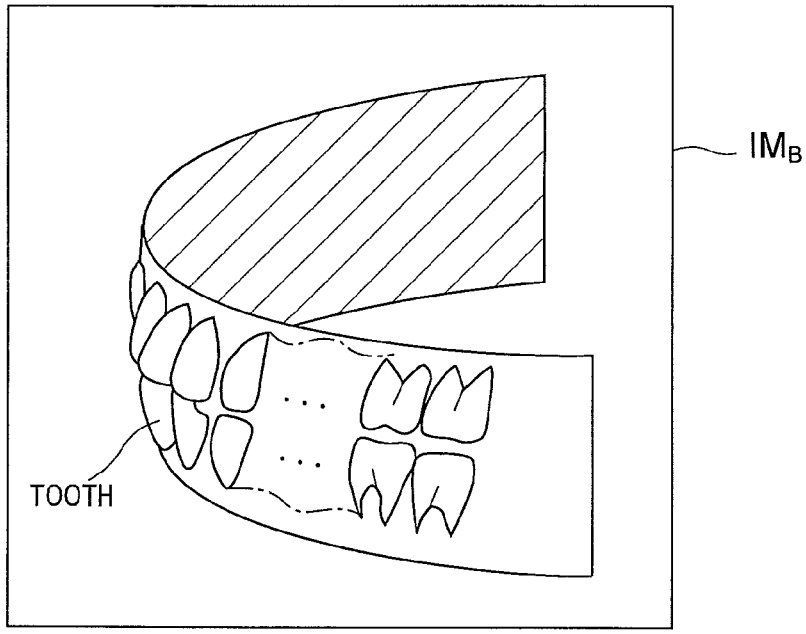
3D AUTOFOCUS IMAGE [ T=T2 ]

FIG.9
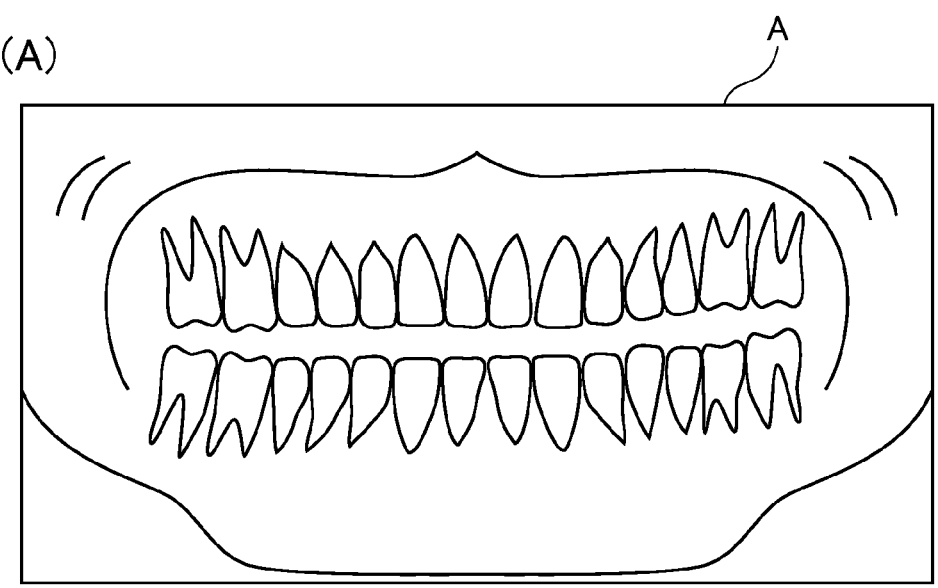
(A)
( T=T1 )
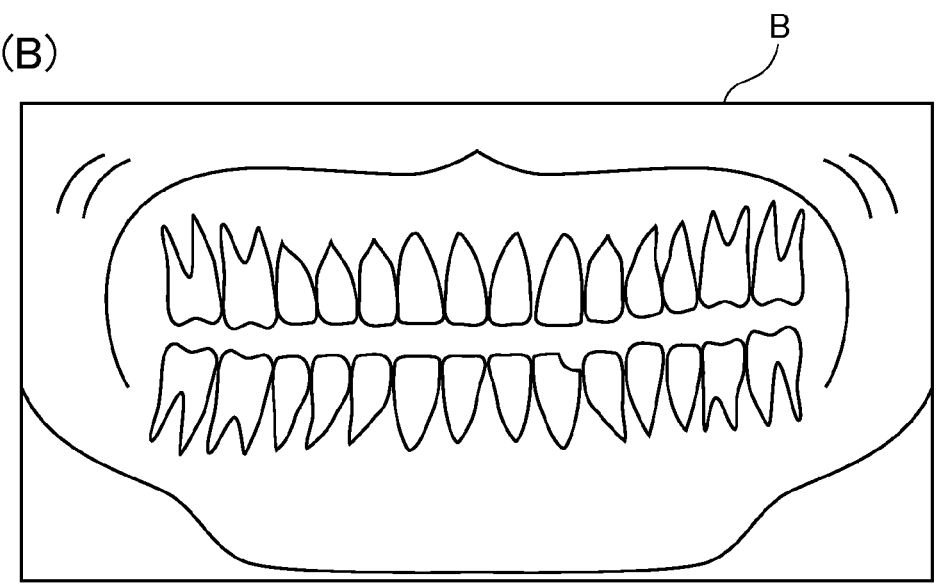
(B)
( T=T2 )

($x_{a0} < x < x_{a4}$)

$(X_{a0} < X < X_{a4})$ (T=T1)

(T=T2)

FIG.17
(A)
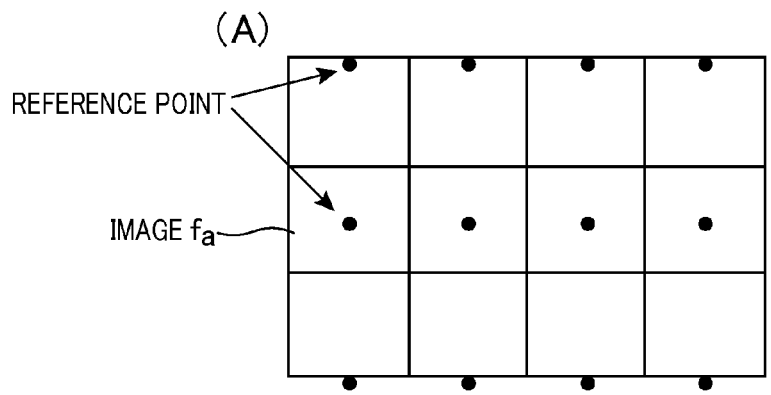
REFERENCE POINT
IMAGE $f_a$
(B)
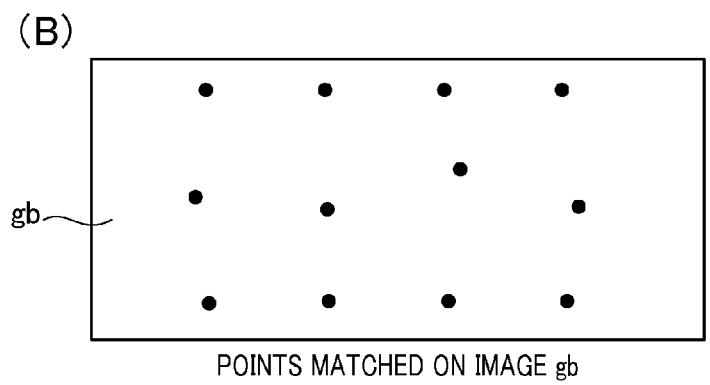
gb
POINTS MATCHED ON IMAGE gb
(C)
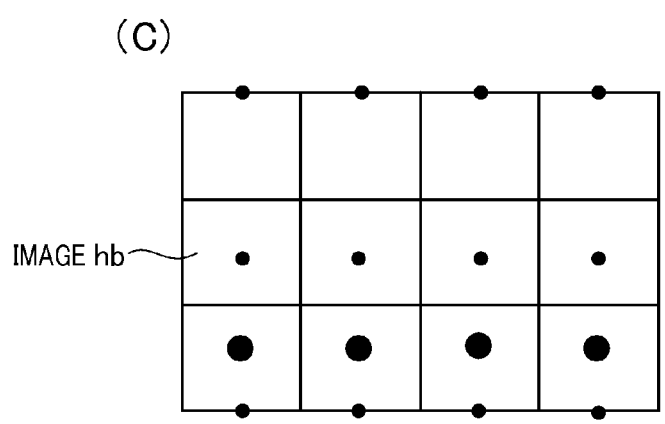
IMAGE hb

VIRTUAL STRAIGHT LINE

FIG.28
(A)
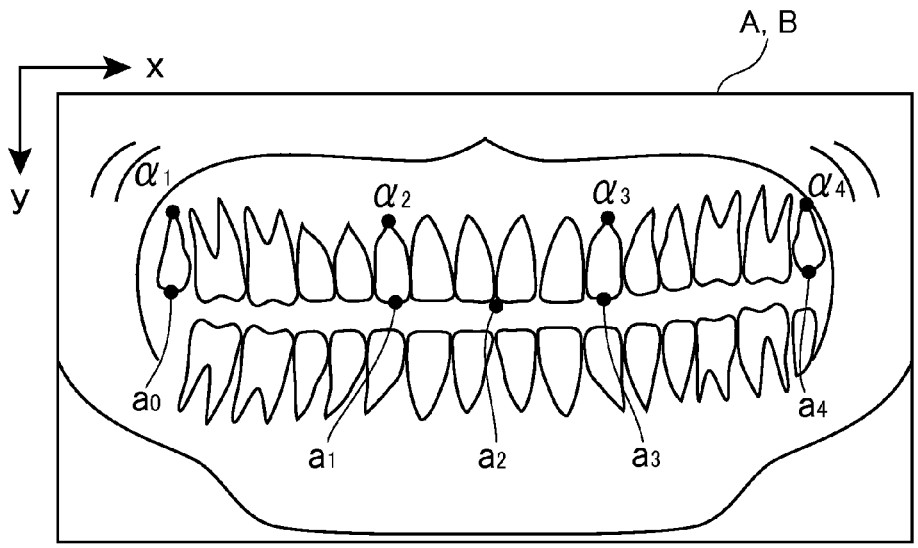
(B)
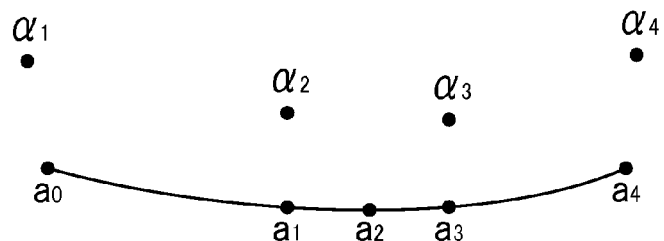
(C)
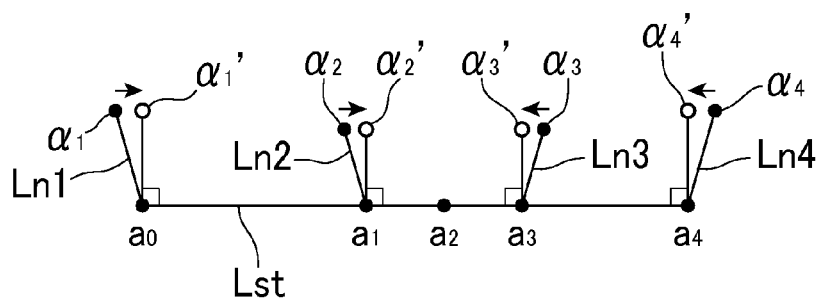

IMAGE PROCESSING APPARATUS AND IMAGE PROCESSING METHOD

CROSS REFERENCE TO RELATED APPLICATIONS

This application is a 371 U.S. National Stage of International Application No. PCT/JP2012/075159, filed Sep. 28, 2012, which claims priority to Japanese Patent Application No. 2011-212543, filed Sep. 28, 2011. The disclosures of the above applications are incorporated herein by reference.

TECHNICAL FIELD

The present invention relates to an image processing apparatus and an image processing method, with which a plurality of planar images of one imaging portion of an object are picked up at different time points and temporal changes of the portion are evaluated from the planar images.

TECHNICAL BACKGROUND

In recent years, an internal structure of an object is imaged using X-ray beams in various fields, such as manufacturing field sites of things, such as semiconductors, construction field sites such as for pipelines, baggage inspection in airports, or medical field sites. In particular, in the field sites of medical research and treatment, what is essential now as one of diagnostic methods is to acquire an internal tomographic image of an object being examined using medical modalities, such as an X-ray imaging apparatus or an X-ray CT.

In conducting an X-ray diagnosis in the medical field sites, it is very important to know how the imaging portion of a patient, as a target of diagnosis, has changed in terms of time. As a matter of course, materials deteriorate with time and accordingly observation of such temporal changes is not limited to patients.

As an algorithm for acquiring information on such temporal changes, Non-patent Document 1 discloses a subtraction method based on a phase-limited correlation method. When the subtraction method is performed, two two- or three-dimensional images are picked up from one portion of an object being examined at different time points. Of the two images, one is used to designate two or three specific positions thereon. Then, positions corresponding to the designated positions are specified on the other two- or three-dimensional image by calculating a strongest phase correlation. In order to mutually align the designated and specified positions of both images, a motion vector (indicating magnification/reduction, rotation or parallel translation) is calculated for each position. Using the motion vectors, one image is aligned with the other image and subtraction between both images is acquired on a pixel basis. Thus, temporal changes of the imaging portion of the object being examined can be acquired from both images.

The subtraction method using the phase-limited correlation method is already used in a device related, for example, to an application filed by the applicant of the present invention in the past (see Patent Document 1).

PRIOR ART REFERENCES

Patent Document 1:
Patent Document: WO 2011016508 A1
Non-Patent Document 1:
"Palm recognition algorithm using phase-limited correlation method, by Koichi ITO et al., Image recognition/interpretation symposium (MIRU 2006), July 2006"

SUMMARY

However, the subtraction method using the phase-limited correlation method requires such calculation as calculation of an amount of phase correlation, calculation of motion vectors, movement of images using the motion vectors, and calculation of subtraction, and accordingly the amount of calculation is quite large. Therefore, the computer that takes up the calculation is required to have high performance. For this reason, this method is problematically difficult to be used in practice such as in medical field sites. For images of comparatively a small range, which are picked up such as in dental X-ray intraoral imaging, this method is appropriate in terms of the amount of calculation and accuracy. However, for dental panoramic images that further cover the entire range of a tooth row, the amount of calculation will be enormous and accordingly this method is inappropriate.

Such a problem has also been prominent, in particular, in the case of the panoramic images acquired by pseudo-three-dimensionally reconfiguring X-ray transmission data using tonnosynthesis (i.e. two-dimensional sectional images that are curved along a tooth row) in the field site of dental treatment.

In the field of dental treatment, such observation of temporal changes is widely required in instances ranging from preventive inspection, such as screening, to treatment associated with implant. However, the enormous amount of calculation implies that it takes time for acquiring the information on the temporal changes. To make up for this, the arithmetic capacity of the computer may be increased, but this is also difficult when the manufacturing cost of the apparatus is concerned.

Further, in the field of medical treatment, magnification factor's being indefinite or image blur is caused by the positioning of a patient or the individual difference in tooth row. Therefore, it would be impossible, by any measure, to interpret the temporal changes of a tooth row of a patient, using panoramic images based on conventional art. If such temporal changes are attempted to be observed, imaging is required to be performed for several times with some interval therebetween. For example, in the case such as of the changes in decay or the treatment associated with implant, imaging is required to be performed before and after the treatment. The same patient is subjected to positioning every time imaging is performed and accordingly, in general, the spatial position of the oral portion will be offset little by little. This is attributed such as to the offset of positioning performed by an operator. However, for the reasons set forth above, it has been nearly difficult in the conventional art to interpret such temporal changes, using panoramic images.

Hence it is desired to provide an image processor and an image processing method, which require only smaller arithmetic capacity in terms of hardware, such as CPU, but are able to provide information related to temporal changes of an imaging portion of an object being examined. Means for Solving the Problems:

As one mode.

an exemplary embodiment provides an image processing apparatus for obtaining difference information between two planar images A and B acquired at two different time points, the planar images being produced based on data indicative of transmission amounts of X-rays transmitted through an object, wherein an X-ray imaging apparatus radiates the X-rays to the object and detects the transmitted X-rays as the data. The image processing apparatus includes first registration means for producing two planar images fa and gb by applying a registration process to overall areas of the two planar images A and B based on curves decided from positions designated on the two planar images A and B respectively, wherein the registration process is performed such that the positions which are set on each of the planar images A and B are aligned along a straight line, both the straight lines corresponding to each other in a horizontal direction, and a scale factor for the registration is changed position by position on the straight lines; second registration means for searching one of the two planar images. gb, produced by the first registration means, for a match of each of a plurality of local regions composing the other planar image fa, to any of regions of the one planar image gb, and re-projecting images of the matched regions to produce a planar image hb; and difference calculating means for calculating the difference information between the planar image hb produced by the second registration means and the other planar image fa produced by the first registration means.

Advantageous Effects

The above embodiment can provide information associated with temporal changes of one imaging portion of a target to be imaged, with a smaller arithmetic capacity being required in terms of hardware, such as CPU.

BRIEF DESCRIPTION OF THE DRAWINGS

In the drawings:

FIG. 8 is a diagram illustrating two 3D autofocus images of a different imaging time point, which are subjected to the subtraction process;

FIG. 9 is a diagram illustrating two planar images prepared from the two 3D autofocus images;

FIG. 17 is a diagram illustrating rearrangement of the matched areas in the other (linearly arranged) planar image;

FIG. 28 is a diagram illustrating image processing, according to the second embodiment.

MODES FOR IMPLEMENTING THE INVENTION

With reference to the accompanying drawings, hereinafter are described some embodiments related to an image processor of the present invention and their modifications.

In the present embodiments, the image processor is functionally integrally implemented in a dental panoramic imaging apparatus using X-ray beams. Accordingly, this panoramic imaging apparatus is specifically described below.

(First Embodiment)

Referring to FIGS. 1 to 18, hereinafter is described an image processor and an image processing method, related to a first embodiment.

The image processor related to the present invention does not necessarily have to be functionally integrated into such an imaging apparatus. For example, the image processor may be provided as a computer which is separate from the imaging apparatus. Such a computer may be dedicated to the image processing related to the present invention, or may concurrently perform different processings. Such a computer may only have to be configured to be given with a plurality of images of one portion of an object to be imaged, which are picked up by an imaging device, and perform image processing related to the present invention with respect to these plurality of images. In the following embodiment, subtraction information is ensured to be acquired as difference information between two images. However, this is only an example. The information may only have to provide "differences" that accompany the changes or the like of disease conditions.

Description will also be provided regarding a mode that effectively uses images that have been subjected to registration processes described later.

Figure 1:
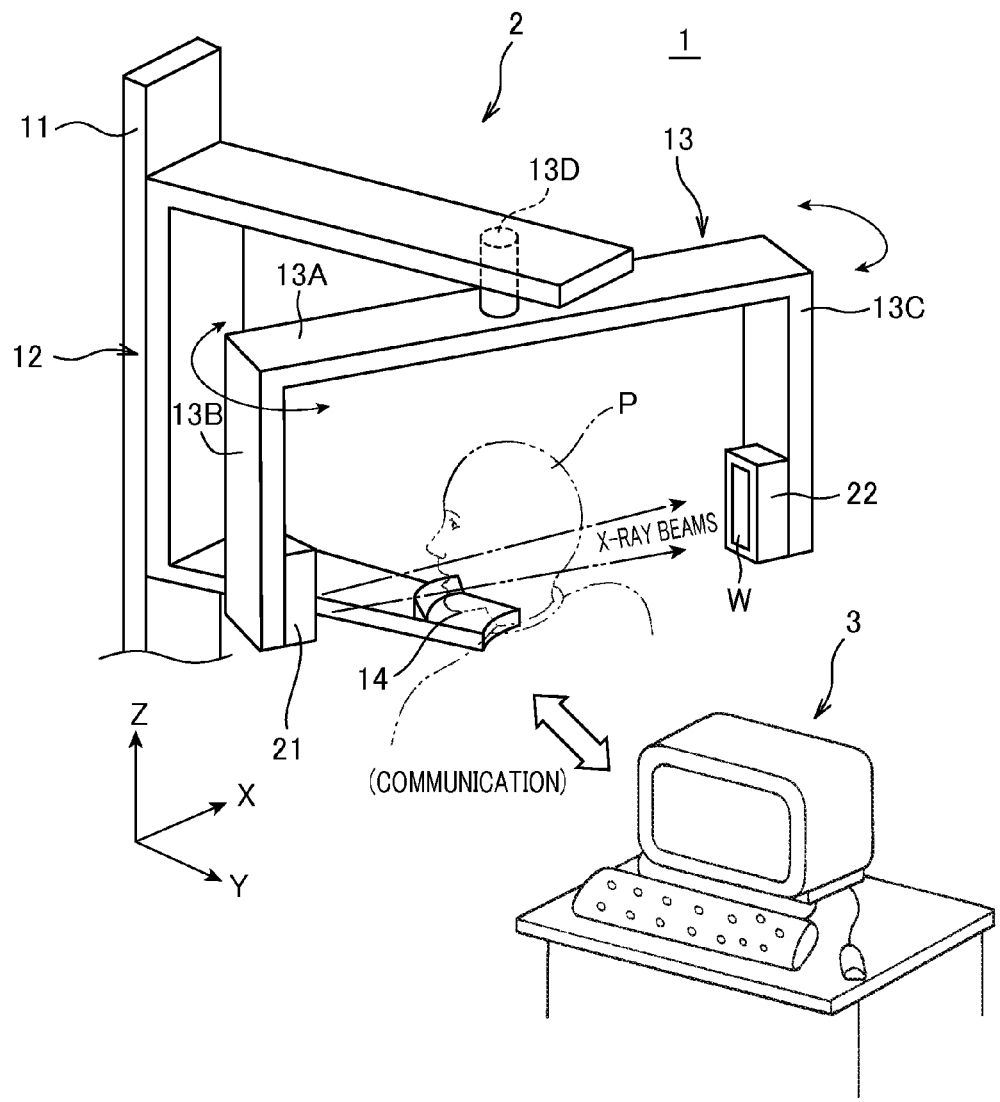
FIG. 1 is a perspective view schematically illustrating a part of a configuration of a panoramic imaging apparatus that uses X-ray beams, into which an image processor is functionally integrated, according to a first embodiment of the present invention.

FIG. 1 is a schematic diagram illustrating a panoramic imaging apparatus 1 having an image processing function related to the first embodiment.

The panoramic imaging apparatus 1 scans the chin portion of an object being examined P with X-ray beams. Using digital X-ray transmission data resulting from the scan, the panoramic imaging apparatus 1 provides 3D (three-dimensional) images (3D autofocus images described later) that identify the actual location and shape of tooth rows having a three-dimensional structure in the chin portion. In particular, the panoramic imaging apparatus 1 has a basic performance of providing information that shows temporal changes between a plurality of (e.g., two) 3D autofocus images picked up at a plurality of temporarily different imaging time points (e.g., two imaging time points with a two-month interval therebetween). The image processing method related to the present invention is performed using tonnosynthesis in the course of acquiring the 3D autofocus images, or in the course of acquiring the information on such temporal changes.

(Embodiments)

Referring to FIGS. 1 to 18, hereinafter is described a preferred embodiment of the panoramic imaging apparatus which functionally integrally installs and performs the image processing and image processing method related to the present invention.

FIG. 1 schematically shows the panoramic imaging apparatus 1. The panoramic imaging apparatus 1 includes a gantry (data acquisition device) 2 that acquires data from the object being examined P, and a console 3 that processes the acquired data to prepare images, while controlling the operation of the gantry 2.

The gantry 2 includes a support pillar 11. A longitudinal direction in which the support pillar extends is referred to as vertical direction (or up-and-down direction: Z-axis direction), and a direction perpendicular to the vertical direction is referred to as a horizontal direction (direction along an X-Y plane). The support pillar 11 includes a substantially U-shaped vertical-movement arm unit 12 which is movable in the vertical direction.

A pivotal arm unit 13 is hung down from the vertical-movement arm unit 12 via a rotary shaft 13D and made rotatably movable about the Z-axis direction by the rotary shaft 13D. The pivotal arm unit 13 includes a horizontal arm 13A substantially having a shape of upside down U, and a radiation-source-side vertical arm 13B and a detection-side vertical arm 13C which extend downward from both ends of the horizontal arm 13A. The rotary shaft 13D uses the output of a drive mechanism, such as an electric motor, not shown. In the figure, reference 14 indicates a chin rest on which the chin of the object being examined P is placed.

The radiation-source-side vertical arm 13B has a lower end portion which is provided with an X-ray tube 21. An X-ray beam radiated as a pulse X-ray beam, for example, from the X-ray tube 21 is collimated by a collimator (not shown) which is also provided at the lower end portion. The collimated X-ray beam then transmits through the chin portion of the object being examined P and propagates to the detection-side vertical arm 13C (see the phantom line). The detection-side vertical arm 13C has a lower end portion which is provided with an X-ray detector 22 (hereinafter referred to as detector) having an X-ray incident window W (e.g., 5.0 mm wide×145 mm high). The detector 22 has a sensor surface having a size, for example, of 6.4 mm wide×150 mm high).

Figure 2:
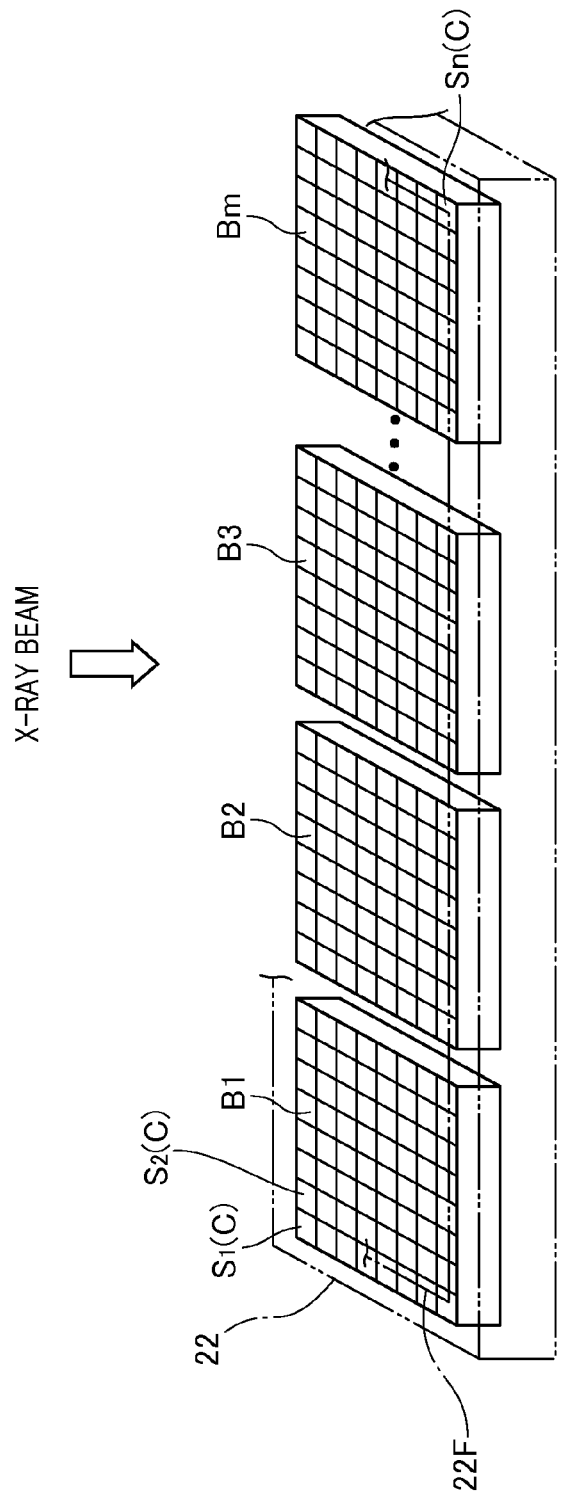
FIG. 2 is a schematic diagram illustrating a detector mounted to the panoramic imaging apparatus.

As shown in FIG. 2, the detector 22 has a plurality of detection modules B1 to Bm in which X-ray imaging elements are two-dimensionally arrayed. The plurality of detection modules B1 to BM as a whole configure a detection part. The plurality of modules B1 to Bm are formed as blocks independent of each other and mounted on a base (not shown), with each block being in a predetermined shape (e.g., rectangular shape), thereby forming the whole detector 22. Each detection module B1 (to Bm) is made of a semiconductor material that directly converts X-ray beams to electric pulse signals. Thus, the detector 22 is a photon counting type X-ray detector based on a direct conversion method using semiconductors.

As mentioned above, the detector 22 is formed as an assembly of the plurality of detection modules B1 to Bm. The detector 22 has acquisition pixels Sn (n=1 to N: the number of pixels N equals, for example, to 50×1450 pixels) which are two-dimensionally arranged in the entirety (see FIG. 2). For example, the size of each acquisition pixel Sn is 200 μm×200 μm.

Thus, the detector 22 counts photons corresponding to incident X-ray beams for each pixel (acquisition pixel) Sn (n=1 to N) configuring the sensor surface of the detector. The detector 22 then outputs electric data reflecting the count at a high frame rate of 300 fps or the like. This data is also called frame data.

Each of the plurality of acquisition pixels Sn is configured by a scintillator, such as a cadmium telluride semiconductor (CdTe semiconductor), a cadmium zinc telluride semiconductor (CdZnTe semiconductor), a silicon semiconductor (Si semiconductor) or Cesium Iodide (CsI), and a photoelectric converter configured by a semiconductor cell (sensor) C, such as a C-MOS. Each of the semiconductor cells C detects incident X-ray beams and outputs a pulsed electric signal according to the energy value. Specifically, the detector 22 includes a group of cells in which a plurality of semiconductor cells C are two-dimensionally arrayed. Further, each of the semiconductor cells C, i.e. each of the two-dimensionally arrayed plurality of acquisition pixels Sn, has an output side provided with a data acquisition circuit 51n (n=1 to N). A path extending from each of the acquisition pixels Sn, i.e. each of the semiconductor cells C, to each data acquisition circuit $51_1$ (to $51_N$) is referred to as an acquisition channel CNn (n=1 to N), as necessary.

The structure of the group of semiconductor cells C is also well known as disclosed by JP-A-2000-069369, JP-A-2004-325183 and JP-A-2006-101926.

The size (200 μm×200 μm) of each acquisition pixel Sn mentioned above is set to a sufficiently small value that enables detection of X-ray beams as photons (particles). In the present embodiment, the size that enables detection of X-ray beams as the particles is defined to be "the size that can virtually ignore the occurrence of superimposition phenomenon (also called pileup) between electric pulse signals responding to a plurality of successive incidences of radiation (e.g., X-ray) particles on the same position or the vicinity thereof, or the size that can predict the amount of the successive incidences". The occurrence of the superimposition phenomenon causes count loss (also called pileup count loss) of X-ray particles in the characteristics of "the number of incidences to actual count" of the X-ray particles. Therefore, the size of each of the acquisition pixels formed in the X-ray detector 22 is set to the size that would not cause or substantially does not cause count loss, or to a level that enables estimation of the amount of the count loss. The detector 22 is characterized in that the detector is capable of correctly measuring the number of X-ray pulses. Therefore, by performing subtraction that is the object of the present invention, the absolute value of the rate of X-ray absorption change can be measured.

Figure 3:
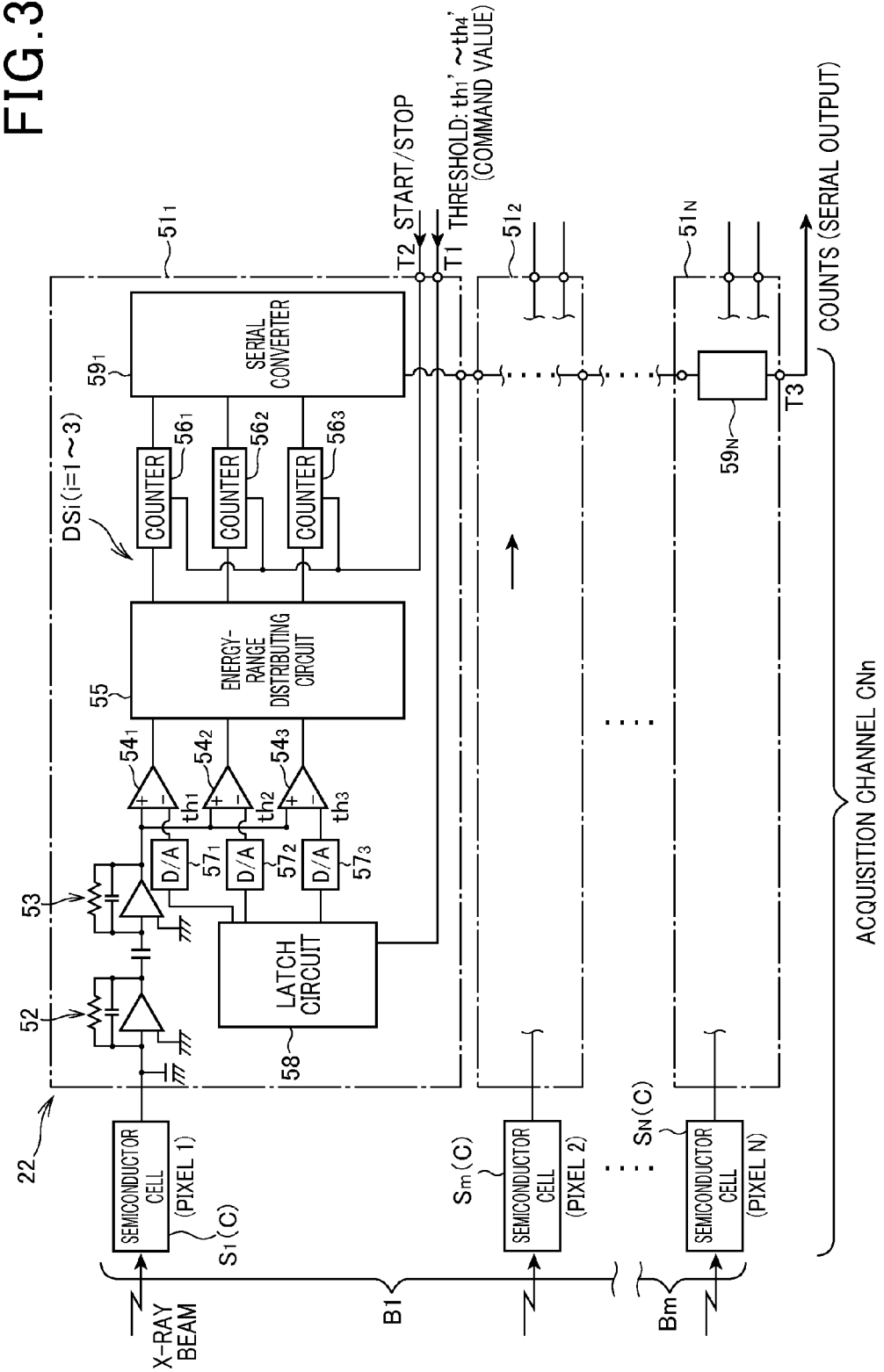
FIG. 3 is a block diagram illustrating an electrical configuration of the detector.

Referring now to FIG. 3, hereinafter is described a circuit electrically connected to the detector 22. Each of the plurality of data acquisition circuits 51n (n=1 to N) has a charge amplifier 52 that receives an analog electric signal outputted from each semiconductor cell C. Downstream of the charge amplifier 52, the data acquisition circuit 51n includes a waveform shaping circuit 53, a multiple-stage comparator $52_1$ to $54_i$ (here i=3), an energy-range distribution circuit 55, multiple-stage counters $56_1$ to $56_i$ (here i=3), multiple-stage D/A converters $57_1$ to $57_i$ (here i=3), latch circuit 58 and a serial converter 59.

Each charge amplifier 52 is connected to a corresponding current-collecting electrode of each semiconductor cell C, charges up charges collected in response to the incidence of X-ray particles and outputs the charges as an electric pulse signal. The charge amplifier 52 has an output terminal connected to the waveform shaping circuit 53 whose gain and offset are adjustable. The waveform shaping circuit 53 shapes the waveform of a detected pulse signal by processing it with the gain and offset that have been adjusted in advance. The gain and offset of the waveform shaping circuit 53 are calibrated, taking account of unevenness with respect to charge characteristics and variation in the characteristics of each circuit, for each acquisition pixel Sn configured by the semiconductor cell C. This can enhance the output of a waveform shaping signal removed with unevenness and enhance the accuracy of setting a relative threshold thereto. As a result, a waveform-shaped pulse signal corresponding to each acquisition pixel Sn, i.e. outputted from the waveform shaping circuit 53 of each acquisition channel CNn, will substantially have characteristics reflecting the energy value of the incident X-ray particles. Accordingly, the variation between the acquisition channels CNn is remarkably improved.

Figure 4:
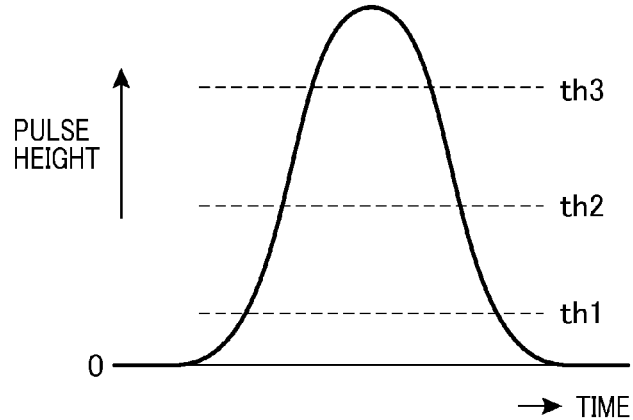
FIG. 4 is a diagram illustrating a relationship between incident X-ray pulse and energy thresholds for energy discrimination.

The waveform shaping circuit 53 has an output terminal connected to the comparison input terminals of the plurality of comparators $54_1$ to $54_3$. As shown in FIG. 4, the plurality of comparators $54_1$ to $54_3$ have respective reference input terminals to which respective analog thresholds $th_i$ (here i=1 to 3) having a different value are applied. Thus, a single pulse signal can be separately compared with the different analog thresholds $th_1$ to $th_3$. The reason for the comparison is to check which of the energy ranges ER1 to ER3 set in advance by being divided into a plurality of divisions the energy value of the incident X-ray particles belongs (is discriminated) to. The peak value (that shows the energy value of the incident X-ray particles) of the pulse signal is determined as to which of the values of the analog thresholds $th_1$ to $th_3$ it exceeds. The energy range to which the peak value is discriminated depends on this determination. Normally, the smallest analog threshold $th_1$ is set as a threshold that ensures not to detect disturbance, or noises caused by circuits, such as the semiconductor cell C and the charge amplifier 52, or low-energy radiation unnecessary for imaging. The number of thresholds, i.e. the number of comparators, is not necessarily limited to three but may be any number, e.g. one including the analog threshold $th_1$, or two or more.

Specifically, the analog thresholds $th_1$ to $th_3$ are provided, in digital values, to each acquisition pixel Sn, i.e. each acquisition channel, from a calibration calculator 38 of the console 3 via an interface 31. Accordingly, the reference input terminals of the respective comparators $54_1$ to $54_3$ are connected to the output terminals of the three D/A converters $57_1$ to $57_3$, respectively. The D/A converters $57_1$ to $57_3$ are connected to a threshold reception terminal $T_1$ (to $T_N$) via the latch circuit 58. The threshold reception terminal $T_1$ (to $T_N$) is connected to the interface 31 of the console 3.

In imaging, the latch circuit 58 latches digital thresholds $th_1'$ to $th_3'$ provided from a threshold providing unit 41 via an interface 31 and the threshold reception terminal $T_1$ (to $T_N$) and outputs the latched thresholds $th_1'$ to $th_3'$ to the D/A converters $57_1$ to $57_3$, respectively. Thus, the D/A converters $57_1$ to $57_3$ are able to provide the instructed analog thresholds $th_1$ to $th_3$, as voltage, to the comparators $54_1$ to $54_3$, respectively. Each acquisition channel CNn is connected to one or more circuit systems which extend from the D/A converter $57_i$ (i=1 to 3) to the counter $56_i$ (i=1 to 3) via the comparator $54_i$ (i=1 to 3). This circuit system is referred to as "discrimination circuit" $DS_i$ (i=1 to 3).

Figure 5:
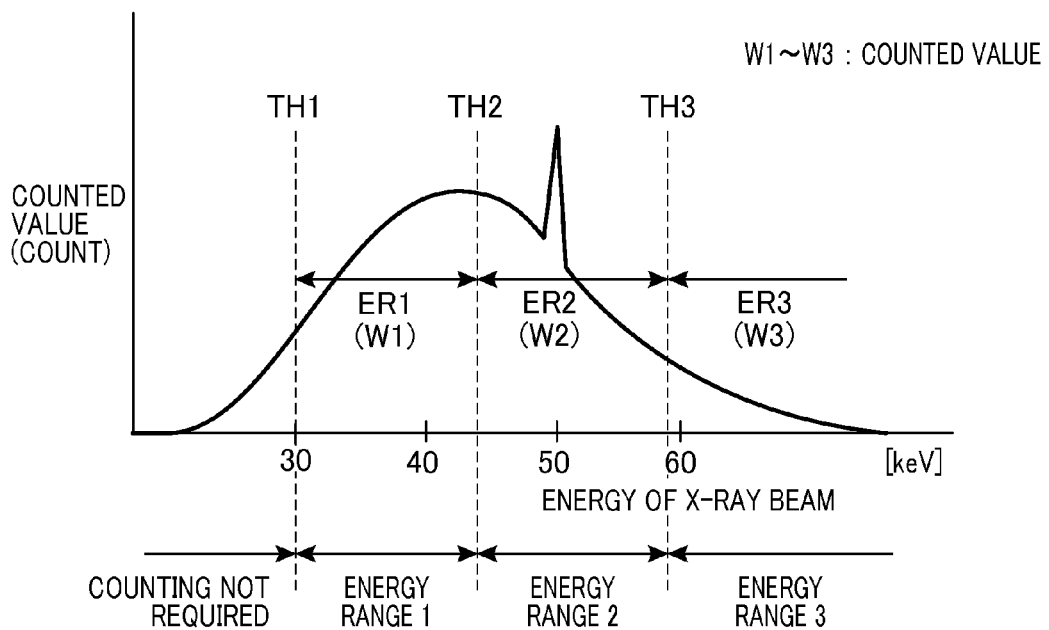
FIG. 5 is a diagram illustrating a relationship between energy distribution of incident X-ray beams, photon count and energy ranges.

FIG. 5 shows an example of setting an energy threshold $TH_i$ (i=1 to 3) equivalent to the analog threshold $th_i$ (i=1 to 3). As a matter of course, the energy threshold $TH_i$ is a discrimination value which is discretely set and can be optionally set by a user.

The analog threshold $th_i$ is an analog voltage provided to the comparator $54_i$ in each discrimination circuit $DS_i$, and the energy threshold $TH_i$ is an analog value for discriminating the X-ray energy (keV) of an energy spectrum. The waveform in FIG. 5 shows an example of a continuous spectrum of the X-ray energy radiated from an X-ray tube. The counted value (count) indicated by the vertical axis is in proportion to the photon occurrence frequency that corresponds to the energy value indicated by the horizontal axis. The energy value of the horizontal axis relies on the tube voltage of the X-ray tube 21. With respect to this spectrum, the first analog threshold $th_1$ is set correspondingly with the energy threshold $TH_1$ that can discriminate a range where measurement of the number of X-ray particles is not necessary (where no meaningful X-ray information is available and where circuit noises are mixed), from a low-energy range ER1. The second and third analog thresholds $th_2$ and $th_3$ are set so as to sequentially provide the second and third energy thresholds $TH_2$ and $TH_3$, each having a higher value than the first energy threshold $TH_1$. Thus, appropriate discrimination points are defined on the basis of the characteristics of the energy spectrum waveform and design values and hence energy ranges ER2 to ER4 are set.

Assuming one or more reference objects being examined, the energy threshold $TH_i$ is determined so that the count in a predetermined period of each energy range will be substantially constant.

Accordingly, as shown in FIG. 3, the output terminals of the comparators $54_1$ to $54_3$ are connected to the energy-range distribution circuit 55. The energy-range distribution circuit 55 interprets the outputs of the plurality of comparators $54_1$ to $54_3$, that is, interprets results of comparison between a pulse voltage corresponding to the energy value of the detected X-ray particles and the analog threshold $th_1$ (to $th_3$), and performs distribution, taking account of which of the energy ranges ER1 to ER3 the energy value is to be classified. The energy-range distribution circuit 55 transmits a pulse signal suitable for the results of discrimination to any one of the counters $56_1$ to $56_3$. For example, if there is an event to be discriminated to the energy range ER1, the energy-range distribution circuit 55 transmits the pulse signal to the first-stage counter $56_1$. If there is an event to be discriminated to the energy range ER2, the energy-range distribution circuit 55 transmits the pulse signal to the second-stage counter $56_2$. The same applies to the energy range ER3.

Each of the counters $56_1$ to $56_3$ counts up a pulse signal every time it is inputted from the energy-range distribution circuit 55. Thus, each of the counters $56_1$ to $56_3$ is able to measure the number of X-ray particles of the energy value discriminated to the corresponding energy range, as an integrated value of each predetermined period. The counters $56_1$ to $56_3$ are provided with start and stop signals from a controller 33 of the console 3 via a start/stop terminal T2. The measurement of the predetermined period is externally managed using a reset circuit possessed by each counter.

In this way, the number of particles of the X-ray beams incident on the detector 22 is measured for each acquisition pixel Sn and for each energy range by the plurality of counters $56_1$ to $56_3$ in the predetermined period before the measurement is reset. The counts of the X-ray particles are parallelly outputted from the counters $56_1$ to $56_3$ as digital count data and then converted to a serial format by the serial converter 59. The serial converter $59_1$ is connected in series with the serial converters $59_2$ to $59_N$ of all of the remaining acquisition channels. Accordingly, all digital count data are outputted from the serial converter $59_N$ of the last channel and transmitted to the console 3 via a transmission terminal T3. In the console 3, the interface 31 receives the count data for storage in a first storage 34.

Then, an image processor 35 reads the count data stored in the first storage 34 in accordance with an instruction of an operator received from an input device 37. Then, using the count data, the image processor 35 reconfigures an X-ray transmission image (panoramic image) of a cross section along a tooth row, for example, on the basis such as of tonnosynthesis. The count data of the plurality of energy ranges ER1 to ER3 are obtained from each acquisition pixel Sn. Accordingly, for example, in reconfiguring the panoramic image, the image processor 35 performs weighting with more weight for the count data having higher energy value, followed by addition of the results. Thus, acquired data are prepared for each acquisition pixel Sn. In this way, the data acquired from all the acquisition pixels Sn accompanying the X-ray scan get together. These acquired data are processed using tonnosynthesis to reconfigure a panoramic image. For example, the panoramic image is displayed by a display 36. As a matter of course, a panoramic image may be reconfigured without performing weighting.

There are a variety of methods for performing weighting. As mentioned above, when a weighting process is performed such that the count data of a higher-energy range are emphasized, the artifacts due to beam hardening can be suppressed. Alternatively, weighting may be performed such that a lower-energy range is emphasized for the purpose of improving the contrast of soft tissue. Alternatively, both of the ranges may be emphasized in weighting, for the purpose of suppressing artifacts due to hardening and improving the contrast of soft tissue.

Reflection of the cervical vertebra, for example, which is superimposed over the shadow of the front tooth portion and is inevitable in a dental panoramic apparatus, can be mitigated to some extent by performing weighting for emphasizing the count data of a higher-energy range when reconfiguring the front tooth portion. The similar weighting process can be used for mitigating the superimposition of the side tooth rows, or for mitigating reflection of opposite-side jaws in performing, so-called, orthogonal imaging. Further, in the case where one desires to have a closer look at the mandibular canal or the like with good contrast, he/she can perform the weighting for emphasizing the count data of a lower-energy range in performing reconfiguration to thereby achieve clearer imaging.

In the present embodiment, the semiconductor cells C and the data acquisition circuits 51n corresponding to the respective N acquisition pixels Sn are integrally configured using CMOSs in an ASIC. As a matter of course, the data acquisition circuits 51n may be configured as a circuit or a device separate from the group of semiconductor cells C.

Figure 6:
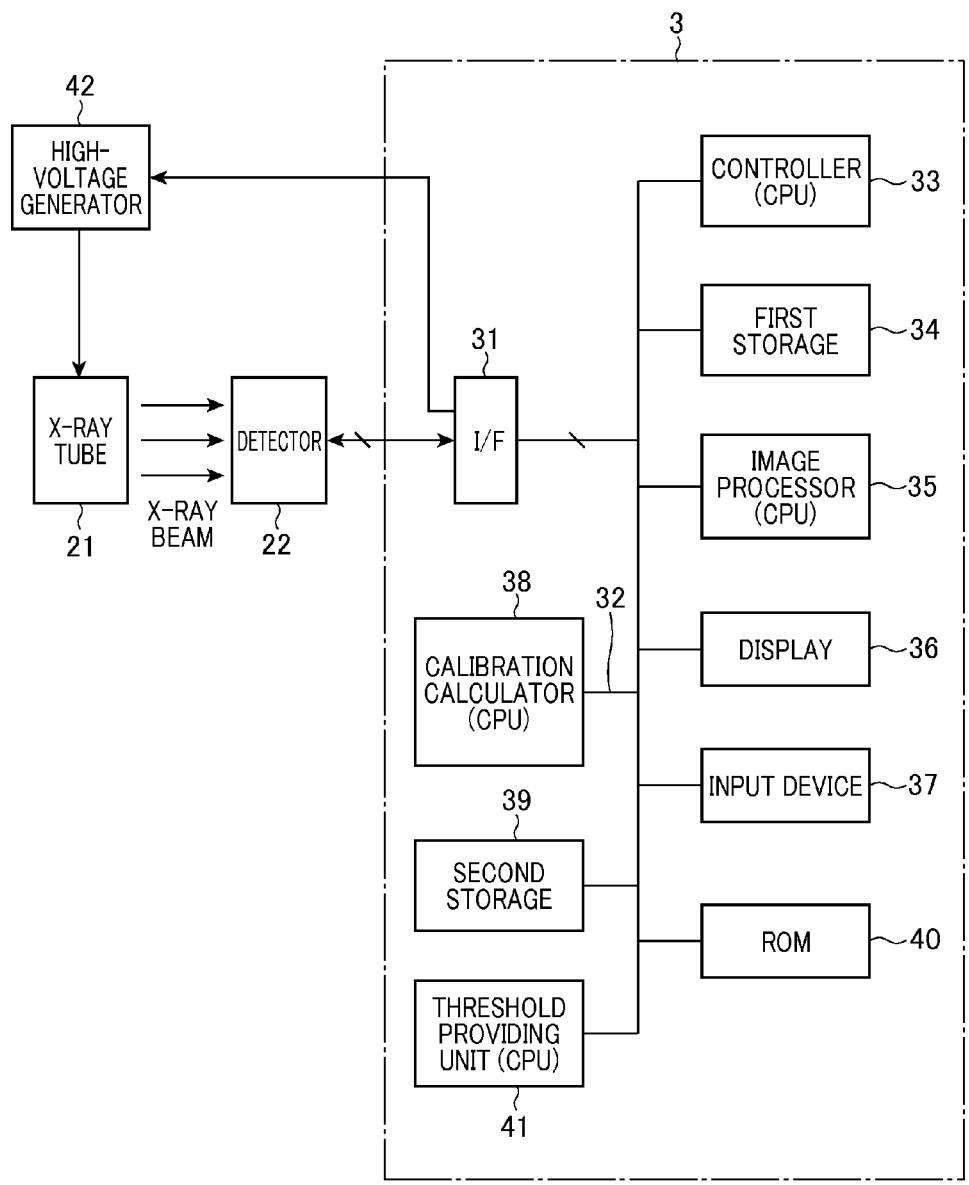
FIG. 6 is a block diagram illustrating an electrical configuration of a consol of the panoramic imaging apparatus.

As shown in FIG. 6, the console 3 includes the interface (I/F) 31 that plays a role of inputting/outputting signals. The console 3 also includes the controller 33, first storage 34, image processor 35, display 36, input device 37, calibration calculator 38, second storage 39, ROM 40 and threshold providing unit 41, which are connected to the interface 31 via a bus 32.

The controller 33 controls the activation of the gantry 2 along a program given in advance to the ROM 40. The control also includes transmitting a command value to a high-voltage generator 42 that supplies high voltage to the X-ray tube 21, and giving an activation instruction to the calibration calculator 38. The first storage 34 stores frame data transmitted from the gantry 2 via the interface 31.

Under the control of the controller 33, the image processor 35 performs various processes on the basis of the program given in advance to the ROM 40. These processes include a process performed for the frame data, in which tonnosynthesis based on a known calculation method called shift and add is performed.

This process enables use of frame data outputted from the detector 22, the frame data being based on the count of the number of X-ray photons acquired for each energy range. Using the frame data, a panoramic image as a tomographic image is prepared such as for a horseshoe-shaped cross section passing through a tooth row in the oral portion of the object being examined P. The horseshoe-shaped cross section can also be a pseudo-three-dimensional cross section. This is because, although the cross section itself is two dimensional, the two-dimensional cross section is three-dimensionally located.

In the present embodiment, this panoramic image is reconfigured using a so-called autofocus method disclosed in WO2011013771. In the autofocus method, automatic and optimum focus is performed to obtain a panoramic image that goes along a desired pseudo-three-dimensional cross section. For example, the desired cross section may be a standard-size cross section set in advance in a tooth row, or may be a cross section obtained at a location by moving forward or backward the standard-size cross section from its position in a depth direction of the tooth row. Alternatively, the desired cross section may be an oblique cross section.

Further, the processes performed by the image processor 35 includes a process of acquiring information on the temporal changes of two panoramic images, for example, that have been picked up at different time points (subtraction process).

The display 36 displays a panoramic image prepared using tonnosynthesis as well as change information acquired through the subtraction process. The display 36 also plays a role of displaying information showing the operating conditions of the gantry 2, and operating information of an operator provided via the input device 37. The input device 37 is used so that an operator can give information necessary for imaging to the system.

The calibration calculator 38 calibrates the digital threshold for energy discrimination, which is given to each energy discrimination circuit of each acquisition pixel Sn in a data acquisition circuit. The second storage 39 memorizes the threshold that has been produced by the calibration for each energy discrimination circuit and for each acquisition pixel.

The threshold providing unit 41 calls up the digital thresholds stored in the second storage 39 in performing imaging, for each acquisition pixel and for each discrimination circuit to transmit the thresholds as command values to the detector 22 via the interface 31. In order to perform this processing, the threshold providing unit 41 executes the program stored in advance in the ROM 40.

The controller 33, the image processor 35, the calibration calculator 38 and the threshold providing unit 41 all include a CPU (central processing unit) that operates in accordance with given programs. The programs are stored in advance in the ROM 40.

Along the procedure shown in FIG. 7, hereinafter is described the subtraction process performed by the image processor 35 in the present embodiment.

Now, the first storage 34 stores pseudo-three-dimensional autofocus images $IM_A$ and $IM_B$ that are picked up at different time points t1 and t2, respectively. For example, there is a time difference of two weeks between the different time points t1 and t2, covering a period, for example, before and after a treatment. For example, as schematically shown in FIG. 8, the autofocus images $IM_A$ and $IM_B$ are pseudo-three-dimensional images of one cross section along a tooth row of a patient.

Figure 7:
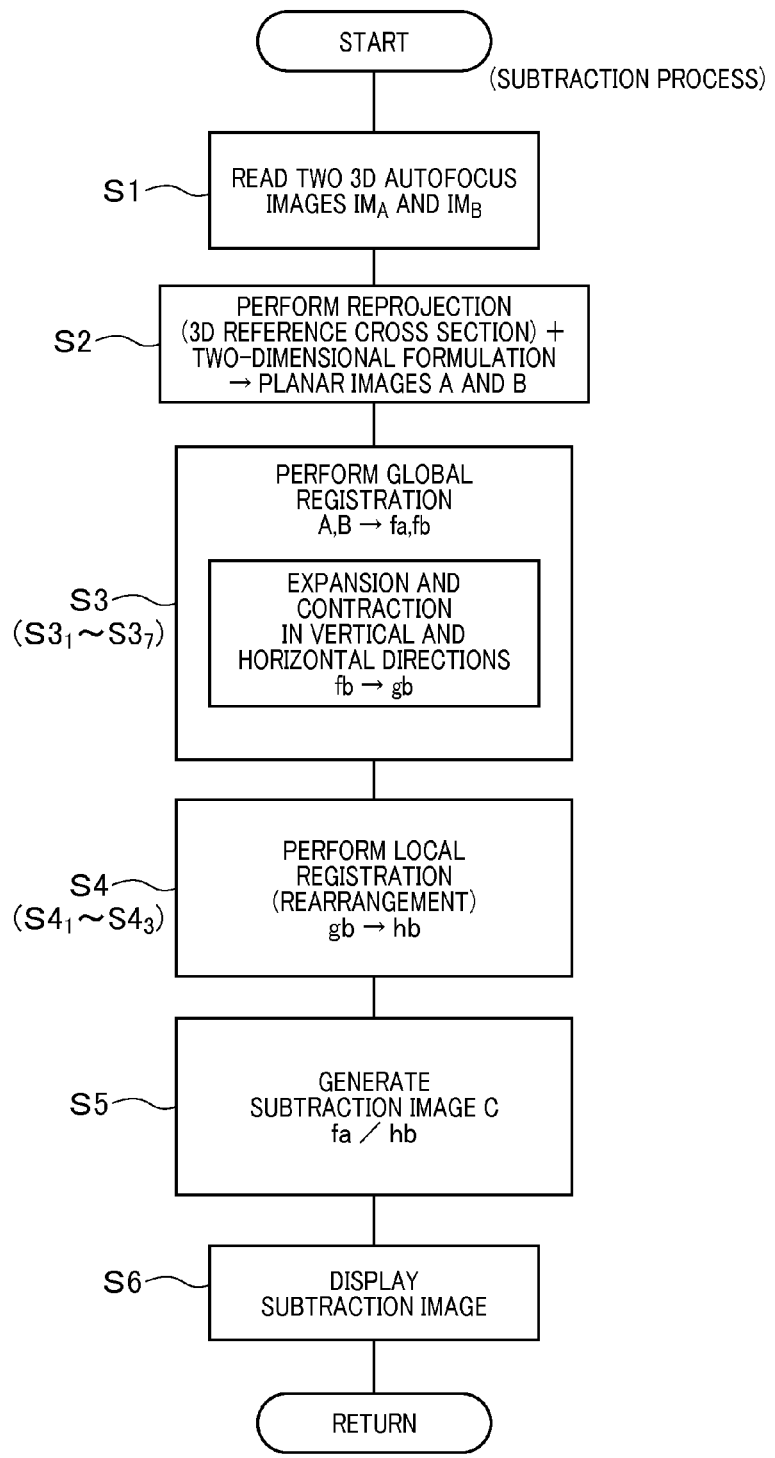
FIG. 7 is a flow diagram schematically illustrating a subtraction process.

At step S1 of FIG. 7, the image processor 35 reads data of the pseudo-three-dimensional autofocus images $IM_A$ and $IM_B$. At step S2, the read data of autofocus images $IM_A$ and $IM_B$ are re-projected to an image along a reference tomographic plane Sref of a tooth row, followed by formulation into two-dimensional planar images A and B.

Then, the image processor 35 subjects the data of the planar images A and B to two-stage registration of global registration (step S3) and local registration (step S4). The registration refers to alignment of both planar images A and B using space conversion. Through the registration, the planar images A and B are converted to registered image data and also converted to aligned images fa and hb, respectively. Subtraction data of the registered images fa and hb are calculated (step S5) and the calculated subtraction data are displayed on the display 36 (step S6). Through the series of steps S3 to S6, the changes that have occurred between the time points t1 and t2 in the chin portion of the patient are imaged, i.e. the temporal changes are formulated into an image.

Hereinafter, steps S3 to S6 are specifically described.

(Global Registration)

From the viewpoint of the amount of calculation and accuracy, it is not practical to immediately perform fine registration. Therefore, the global registration is firstly performed to roughly register the planar mages A and B, and then the local registration is performed to finely align both images. The global registration is performed by the image processor 35 at steps $S3_1$ to $S3_6$ (see FIG. 7) provided below.

Figure 10:
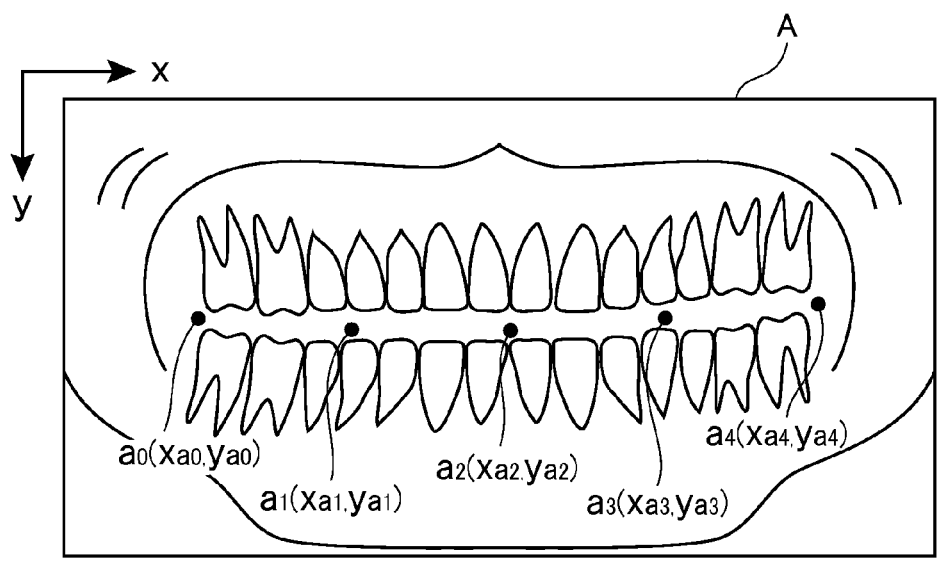
FIG. 10 is a diagram illustrating a state where a plurality of points are plotted, as control points, on one planar image.
Figure 11:
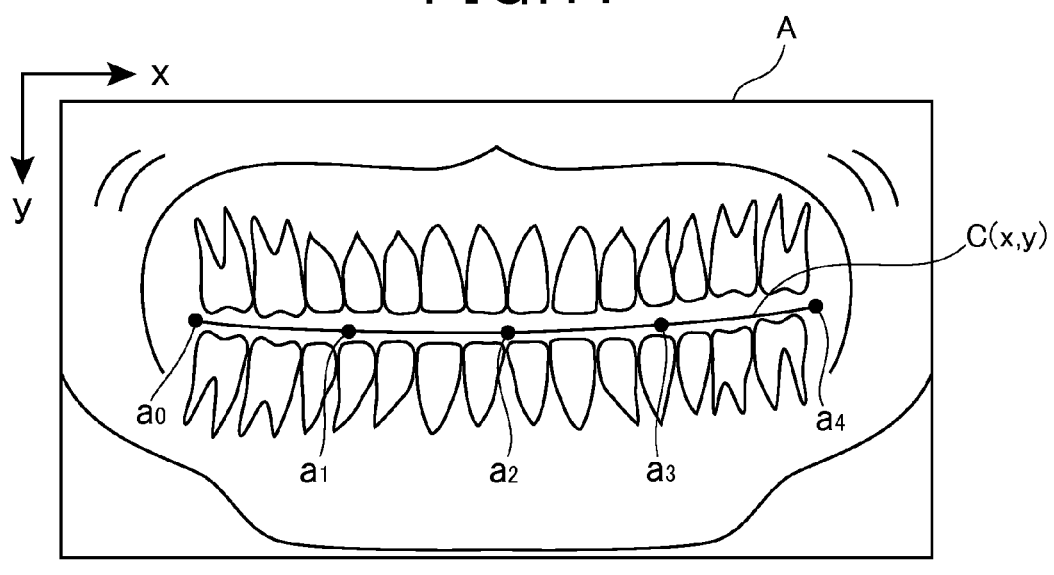
FIG. 11 is a diagram illustrating a state where a curve is set, smoothly connecting the plotted points in the one planar image.
Figure 12:
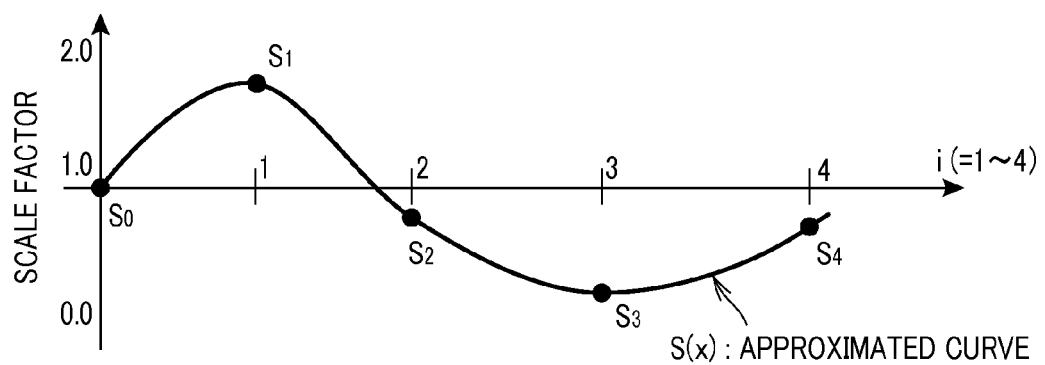
FIG. 12 is a diagram illustrating a curve that shows changes for each position on the horizontal axis, at an expansion ratio used for scaling.
Figure 13:
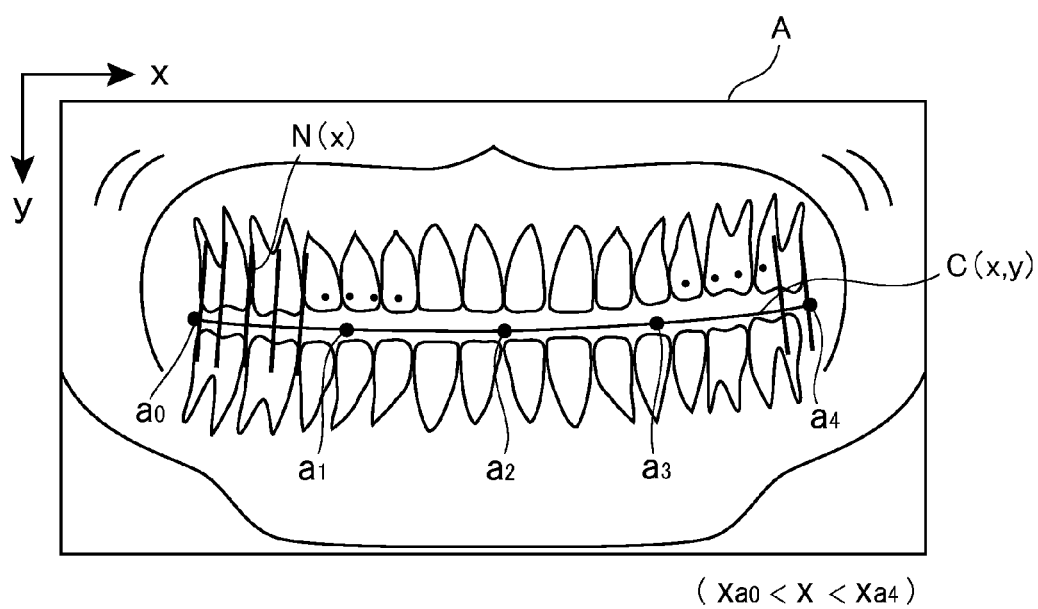
FIG. 13 is a diagram illustrating normal lines set at respective positions on the curve that has been set in the one planar image.

Step $S3_1$: With respect to the two-dimensional planar images A and B, an operator plots five points (hereinafter referred to as control points) $a_0(x_{a0}, y_{a0})$, $a_1(x_{a1}, y_{a1})$, $a_2(x_{a2}, y_{a2})$, $a_3(x_{a3}, y_{a3})$ and $a_4(x_{a4}, y_{a4})$, for example, using the input device 37, such as a mouse. As shown in FIG. 10, as an example, the control points are set at regular intervals along a curved portion between the upper and lower tooth rows. FIG. 10 shows plotting of the control points with respect to only one planar image B, but the five control points are similarly plotted with respect to the other planar image A.

Step $S3_2$: Then, using the Lagrange equation, a curve C (x, y) connecting between the control points $a_0(x_{a0}, y_{a0})$, $a_1(x_{a1}, y_{a1})$, $a_2(x_{a2}, y_{a2})$, $a_3(x_{a3}, y_{a3})$ and $a_4(x_{a4}, y_{a4})$ is calculated so as to fall within a range of $x_{a0}<x<x_{a4}$ (see FIG. 11).

Step $S3_3$: Then, for each of the control points $a_0$ to $a_4$ on the planar image fa, a curved line segment (width) between each control point $a_0$ (to $a_4$) and the next control point $a_1$ (to $a_4$) is rendered to be a reference value 1. Then, with respect to this reference value 1, that of the planar image fb is calculated to find out a scale factor. As a result, discrete points are obtained with scale factors as shown by the black circles in FIG. 12. A curve connecting between the discrete points is approximated using the Lagrange curve. In the approximated curve, position i in the horizontal-axis direction expresses a scale factor of each position (every pixel) in the horizontal-axis (x-axis) direction of the planar image B, relative to the planar image A. Thus, a scale factor in the horizontal-axis direction for each pixel is obtained from the approximated curve and memorized.

Step $S3_4$: Then, a plurality of normal lines N (x) perpendicular to the calculated curve C (x, y) are calculated (see FIG. 13). For example, the length of each normal line corresponds to 50 pixels on the upper side of a control point and 400 pixels on the lower side thereof. The normal line N (x) is expressed by:

$$N(x)=[f(x,y_0), f(x, y_1), \ldots, f(x, y_{m-1})]$$

where $y_0$ to $y_{m-1}$ are values of y-coordinate on the normal line, and a limitation of $x_{a0}<x<x_{a4}$ is required.

Step $S3_5$: Then, the calculated plurality of normal lines N (x) are mapped straight in the horizontal direction, i.e. x-axis direction. As a result, the planar image fa after the global registration is obtained for one planar image A, as follows (see FIG. 14):

$$fa=[N(x_{a0})N(x_{a1}+1) \ldots N(x_{34})]$$

Figure 14:
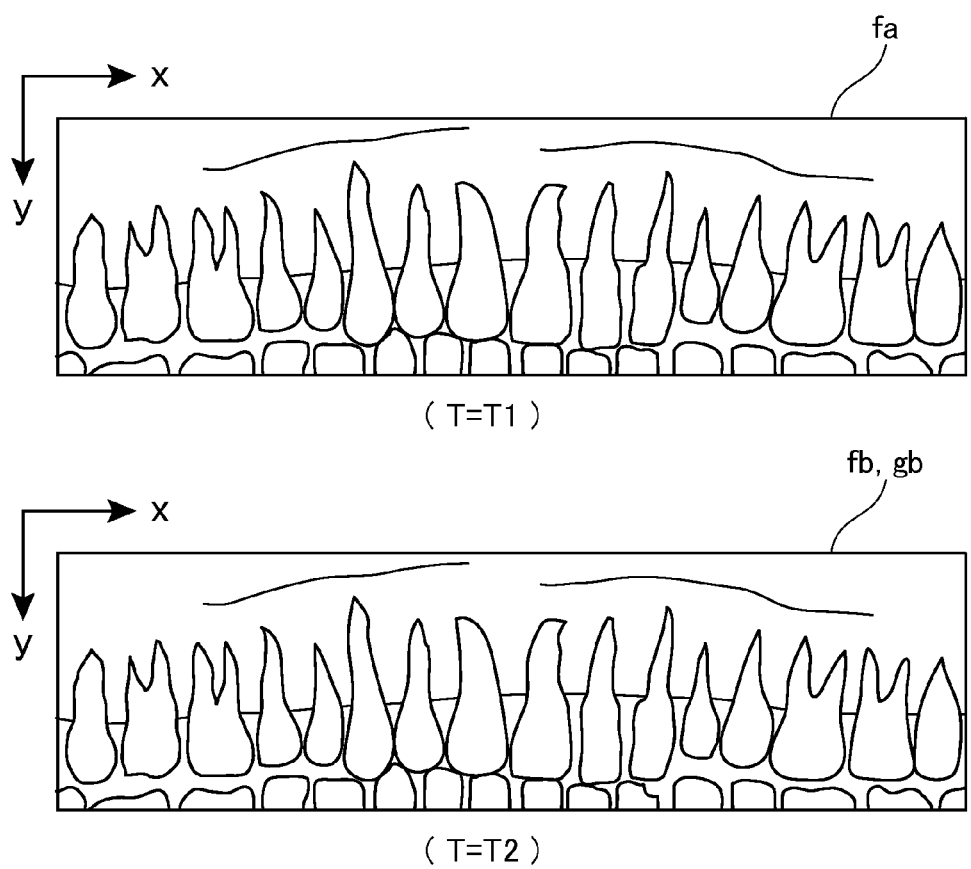
FIG. 14 is a diagram illustrating two planar images prepared by laterally and linearly arranging pixels that go along each of the normal lines, with an expansion ratio being mutually matched in horizontal and vertical directions.
Figure 15:
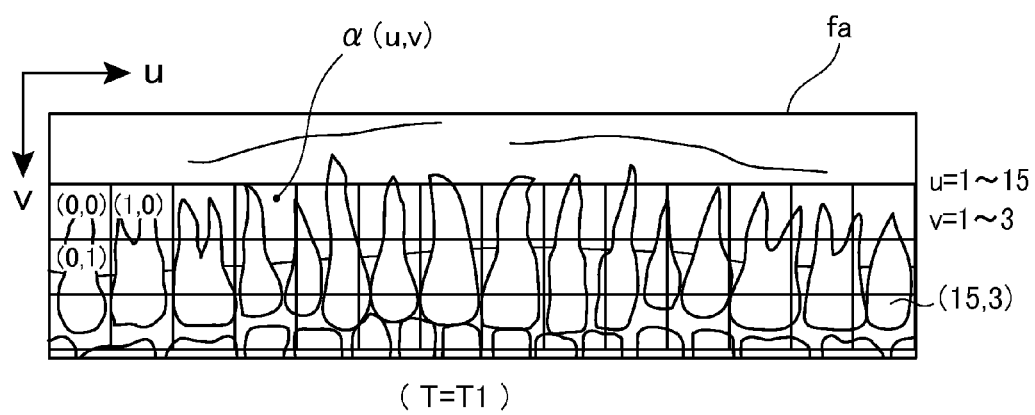
FIG. 15 is a diagram illustrating a state where one of the two linearly arranged planar images is divided into ROIs.
Figure 16:
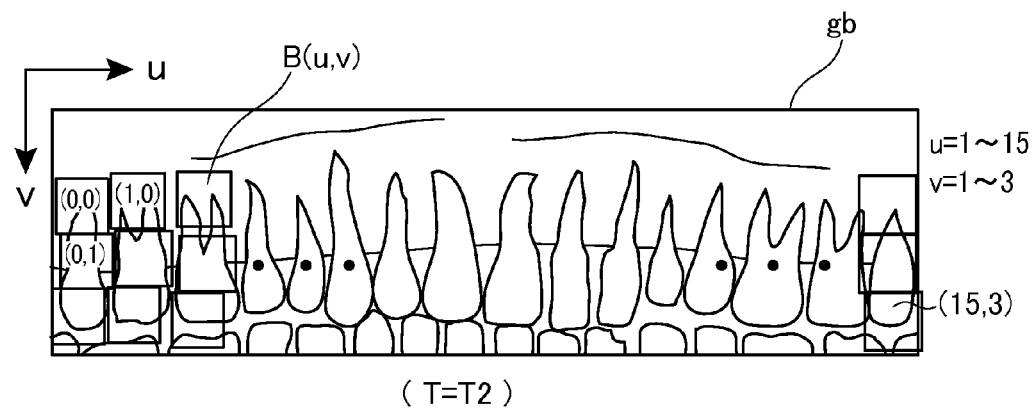
FIG. 16 is a diagram illustrating areas in the other of the two linearly arranged planar images, the areas being matched to the ROIs.

The global registration is similarly performed for the other planar image B to thereby obtain the planar image fb (see FIG. 14).

Step $S3_6$: Further, in conformity with the scale factor already obtained for each position, one planar image fb is expanded or contracted in the horizontal-axis (x-axis) direction.

Step $S3_7$: The planar image fb that has been expanded or contracted in the horizontal-axis direction is also expanded or contracted in the vertical-axis (y-axis) direction using the scale factor of each position. Through the steps $S3_6$ and $S3_7$, the scale of planar image fb is adjusted to thereby produce a final planar image gb applied with the global registration (see FIG. 14).

(Local Registration)

Further, subsequent to the global registration, the local registration is performed. The local registration is performed between one planar image fa after the global registration and the other planar image gb after the global registration including the adjustment of scale factor in vertical and horizontal directions. The local registration is also performed by the image processor 35. The details are shown in steps $S4_1$ to $S4_3$ (see FIG. 7).

Step $S4_1$: First, in accordance with an interactive operation with an operator, the image processor 35 divides one planar image fa in mesh α (u, v) (e.g., u=1, 2, . . . , 15; v=1, 2, 3). Then, the image processor 35 sets each cell of the mesh α (u, v) as a fixed ROI (see FIG. 15), while memorizing a specified position in each ROI as a reference point. For example, for three-row ROIs, the reference point in each ROI in the first row is at the upper end center, the reference point in each ROI in the second row is at the center point, and the reference point in each ROI in the third row is at the lower end center (see (A) of FIG. 17).

Step $S4_2$: Then, the image processor 35 calculates which of the positions (areas) in the other planar image gb each ROI set in one planar image fa corresponds to. To this end, the image processor 35 repeatedly calculates Zero-mean Normalized Cross-Correlation $R_{ZNCC}$, while moving in a search range set in the planar image gb (see FIG. 16). The Zero-mean Normalized Cross-Correlation $R_{ZNCC}$ is calculated through the following formula.

$$R_{ZNCC} = \frac{\sum_{j=0}^{N-1}\sum_{i=0}^{M-1}((\beta(i,j)-\overline{\beta})(\alpha(i,j)-\overline{\alpha})}{\sqrt{\sum_{j=0}^{N-1}\sum_{i=0}^{M-1}(\beta(i,j)-\overline{\beta})\times\sum_{j=0}^{N-1}\sum_{i=0}^{M-1}(\alpha(i,j)-\overline{\alpha})}}$$

where N=height of template and M=width of template.

The Zero-mean Normalized Cross-Correlation $R_{ZNCC}$ is a value that ranges from −1 to +1. When $R_{ZNCC}$=1 is established, it means that the image of a ROI set in one planar image fa completely coincides with the image in a searched area of the other planar image gb.

In finding the corresponding position, the Zero-mean Normalized Cross-Correlation does not necessarily have to be used. Instead, a registration method for a basic two-dimensional image, such as phase-limited correlation, may be used to calculate the corresponding position, although the amount of calculation will be increased.

The search range to be set in the other planar image gb is set for each ROI set in one planar image fa, as an area having a high probability of including the area corresponding to the ROI. This is because, when the other planar image gb as a whole is searched, the amount of calculation will be increased. In order to suppress this, the search range of a predetermined size is set. For example, if the size of a ROI is 100×110 pixels, the size of the search range is 160×190 pixels. The size of the ROI and the search range may be determined according to the contents of a targeted image.

At this step, for each ROI on one planar image fa, an area having a maximum value of the Zero-mean Normalized Cross-Correlation $R_{ZNCC}$ is determined, and a point corresponding to the reference point set on the one planar image fa is set in the other planar image gb. This setting is repeatedly performed for each ROI. This is shown, for example, by black circles in (B) of FIG. 17.

If the Zero-mean Normalized Cross-Correlation $R_{ZNCC}$ has a value=not more than a predetermined value (e.g., 0.9 or more), the ROI may be regarded to sufficiently match the area (area having the same size as that of the ROI) calculated this time and residing in the search range.

On the other hand, if a relationship $R_{ZNCC}$=less than the predetermined value is established, it is determined that the degree of correlation is too low to determine the match to be sufficient. In this case, the image processor 35 determines the set area to be ineffective. The image processor 35 then performs linear interpolation of the movements of the both effective adjacent areas to obtain the position information of the area determined to be ineffective in the planar image gb.

Step $S4_3$: Then, the image processor 35 arrays, i.e. rearranges, pixel values on the basis of the corresponding points found on the other planar image gb. Thus, as shown in FIG. 17 by (C), a rearranged planar image hb is produced.

(Acquisition and Display of Subtraction Information)

After completing the registrations as described above, at step S5, the image processor 35 calculates a subtraction data D(i, j) on the basis of:

$$D(i,j)=\log\{Ar(i,j)/Br(i,j)\}$$

where Ar(i, j) indicates each pixel value in one planar image fa and Br (i, j) indicates each pixel value in the other planar image hb.

Figure 18:
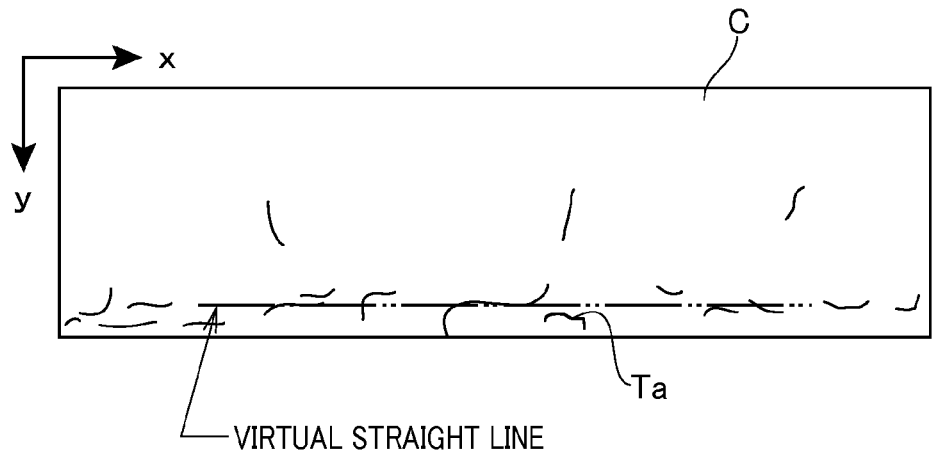
FIG. 18 is a diagram schematically illustrating a subtraction image showing subtraction information as difference information.

Further, the display 36 displays a subtraction image C based on the subtraction data D(i, j). An example of the display is shown in FIG. 18. As shown in the figure, the subtraction image C delineates information Ta that corresponds to the changes between the imaging time points t1 and t2.

As described above, the panoramic imaging apparatus related to the present embodiment is able to further reduce the arithmetic capacity required in terms of hardware, such as CPU, but is able to provide the information associated with the temporal changes of one imaging portion targeted to be imaged.

Specifically, temporal changes in decay or pyorrhea can be evaluated. Temporal changes can be traced for an embedded site of an embedded object that has been provided during implant treatment. Further, the lesion in a tooth root portion can be delineated with high sensitivity. Furthermore, the degree of erosion of the bone that supports a tooth row can be grasped with high sensitivity and in a quantitative way. On the other hand, the decay or the like in a portion where the side teeth are superimposed with each other can also be detected, which detection has been disabled in the panoramic image based on conventional art. In addition, the information as to which of the superimposed teeth the lesion, such as decay, resides in can also be provided by the tomographic position information used in performing autofocus.

The subtraction process can give extremely effective information to a medical doctor or a laboratory technician when he/she makes a diagnosis. For example, interactive image reading can be conducted between the apparatus and an image interpreter. Accordingly, the apparatus plays a great role not only in the currently conducted medical treatment, but also in the aspect of preventive medicine, such as periodic dental checkup.

(Modifications)

The image processor and the image processing method related to the present invention are not necessarily limited to the foregoing embodiment, but may be developed into various modes as in the modifications set forth below.

(First Modification)

A first modification relates to the way of setting the target area for which the Zero-mean Normalized Cross-Correlation $R_{ZNCC}$ is calculated at step $S4_2$ in the local registration described above. An example of this is described referring to FIGS. 19 and 20.

Figure 19:
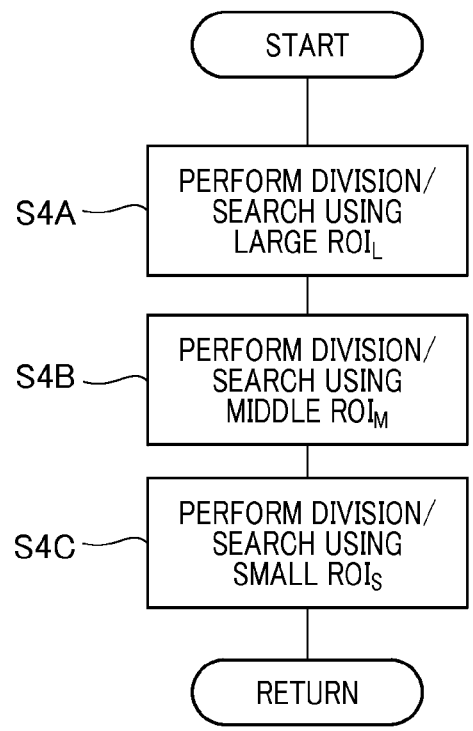
FIG. 19 is a flow diagram illustrating a process that uses large, middle and small ROIs in global registration, according to a first modification.
Figure 20:
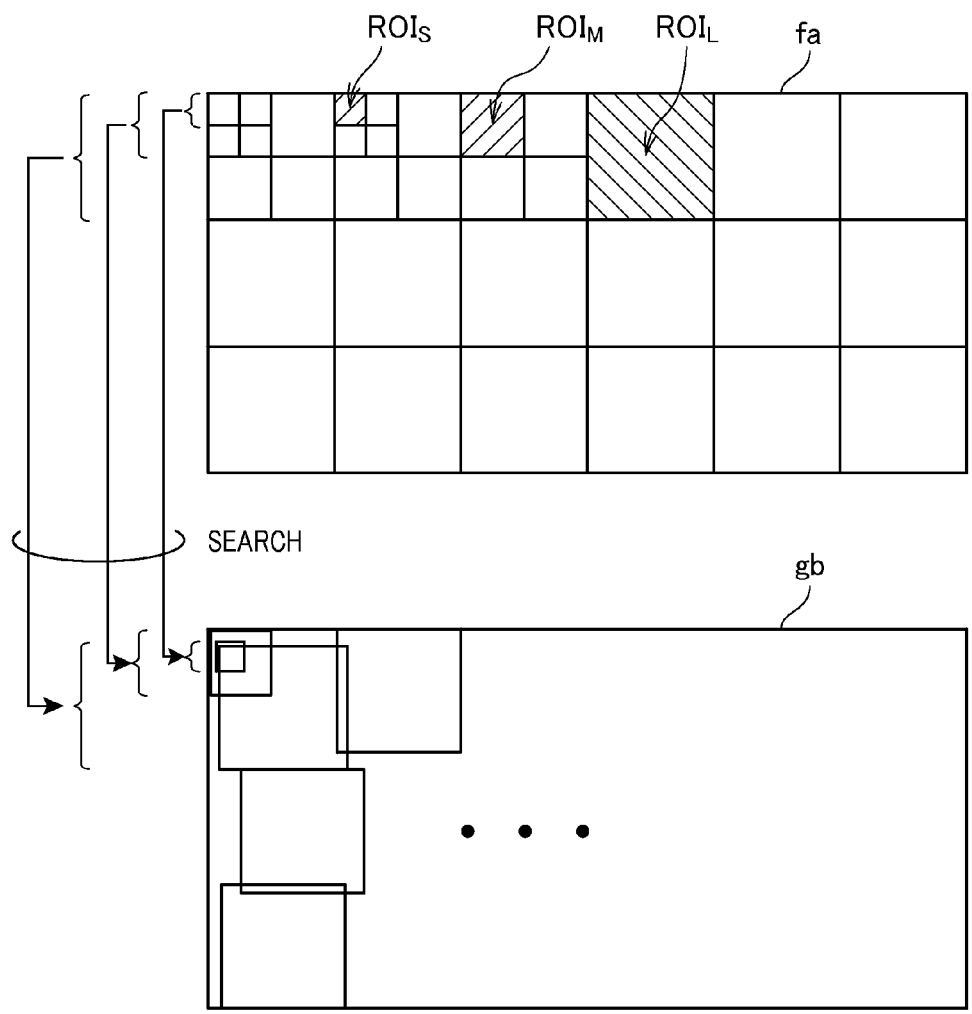
FIG. 20 is a diagram illustrating setting of the large, middle and small ROIs of the first modification and search of areas corresponding to the ROIs.

As shown in FIG. 19, the image processor 35 performs three-stage narrow-down search using three types of ROIs, i.e. large middle and small ROIs: $ROI_L$, $ROI_M$ and $ROI_S$, having a different pixel size. The large $ROI_L$ corresponds to a pixel of 100×110 size or the like, the middle $ROI_M$ corresponds to a pixel of 50×55 size or the like and the small $ROI_S$ corresponds to a pixel of 25×28 size or the like.

First, using the large $ROI_L$, one planar image fa is divided. Then, while areas each corresponding to the $ROI_L$ is being set in the other planar image gb, an area is searched, in which the match based on the foregoing Zero-mean Normalized Cross-Correlation $R_{ZNCC}$ is the best (step S4A). This search is performed for each of the plurality of $ROI_L$s that are the divisions in one planar image fa. In performing the search, a search range may be limited on the planar image gb.

Then, the image processor 35 divides one planar image fa using the middle $ROI_M$. Then, in the other planar image gb, while areas each corresponding to the $ROI_M$ is being set in the vicinity of the area (inside of the area, or an end portion of the area, or a portion beyond the end portion) that has been searched as having the best match with the large $LOY_L$, an area is searched, in which the match based on the foregoing Zero-mean Normalized Cross-Correlation $R_{ZNCC}$ is the best (step S4B). This search is performed for each of the plurality of $ROI_M$s that are the divisions in one planar image fa.

Then, the image processor 35 divides one planar image fa using the small $ROI_S$. Then, in the other planar image gb, while areas each corresponding to the $ROI_S$ is being set in the vicinity of the area (inside of the area, or an end portion of the area, or a portion beyond the end portion) that has been searched as having the best match with the large $LOY_M$, an area is searched, in which the match based on the foregoing Zero-mean Normalized Cross-Correlation $R_{ZNCC}$ is the best (step S4C). This search is performed for each of the plurality of $ROI_S$s that are the divisions in one planar image fa.

As a result, based on the searched areas for the small $ROI_S$, points corresponding to the reference points that have been set in one planar image fa are set in the other planar image gb. The processing after this is similar to the one described above.

In the first modification as well, the advantageous effects similar to those of the image processing in the foregoing embodiment can be obtained. In addition, since an area is narrowed down to an area having a higher degree of match, by gradually reducing the size of a ROI, the accuracy is more enhanced in the match between the two planar images to be compared to each other.

In changing the size of a ROI, two types of ROI, i.e. a large ROI and a small ROI, may be used, or four or more sizes of ROI may be used.

(Second Modification)

A second modification relates to the number of panoramic images targeted to extract the information on temporal changes.

In the foregoing embodiment, two 3D autofocus images are used as targets of extracting temporal changes. Alternatively, three or more 3D autofocus images picked up at three different time points may be used as targets. In this case, extraction of temporal changes is firstly performed between the first and second 3D autofocus images, and then, extraction of temporal changes is performed between the second and third 3D autofocus images. This enables acquisition of the information on the temporal changes during the period from the second to third imaging time points.

(Third Modification)

A third modification relates to the way of showing the image that contains the information on changes.

As shown in FIG. 10, normally, a medical doctor most often performs image interpretation, referring to a panoramic image in which tooth rows are delineated being curved. In other words, a medical doctor is most accustomed to perform image interpretation using a panoramic image of curved tooth rows.

Figure 21:
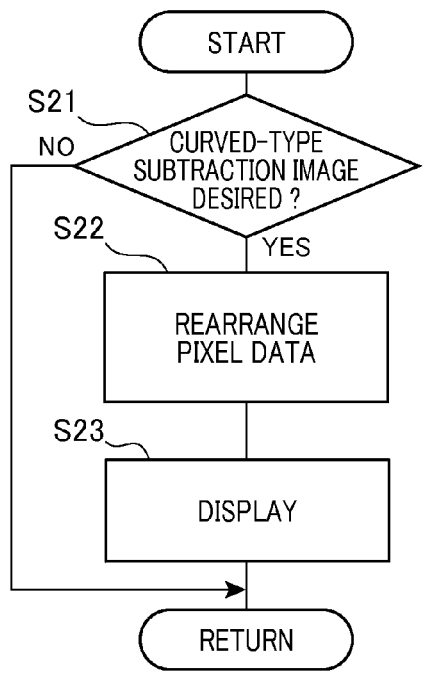
FIG. 21 is a flow diagram illustrating rearrangement from a linear type subtraction image to a curved type subtraction image, according to a third modification.
Figure 22:
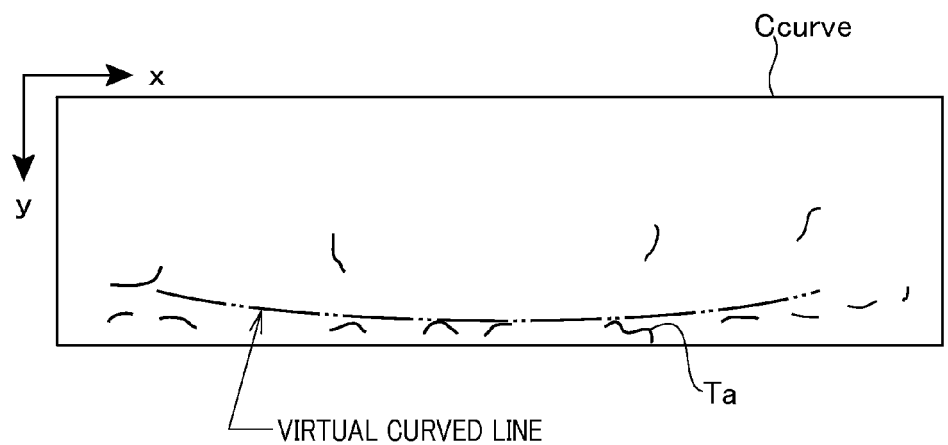
FIG. 22 is a schematic diagram illustrating a curved type subtraction image, according to a third modification.

Thus, a medical doctor may desire to acquire a tooth-row-curved-type subtraction image $C_{curve}$ from a tooth-row-linear-type subtraction image C (step S21 of FIG. 21). In this case, the image processor 35 uses, as a basis, the information on positional relationship of the corresponding points to reversely arrange the pixel data of the tooth-row-linear-type subtraction image C into pixel data of the tooth-row-curved-type subtraction image $C_{curve}$ (step S22). Further, as shown in FIG. 22, the image processor 35 displays the subtraction image $C_{curve}$ on the display 36 (step S23).

In this way, the medical doctor is able to perform image interpretation, referring to a familiar tooth-row-curved-type image and accordingly the work of the medical doctor is reduced.

From another viewpoint, performing conversion to a tooth-row-linear-type image and performing correct registrations imply that tooth rows are normalized and arranged on an individual-person basis every time the conversion and registrations are performed. In extracting the characteristics of an image from a different perspective as well, performing the conversion and the registrations may simplify the extraction algorithm and would expand the application range.

(Fourth Modification)

According to the foregoing embodiment, the two 3D autofocus images $IM_A$ and $IM_B$, which are targeted to extract the information on changes using subtraction, are subjected, as they are, to the subtraction process as described above. However, as the fourth modification, preprocessing may be performed for the subtraction process to roughly align the two 3D autofocus images $IM_A$ and $IM_B$ beforehand in a 3D space, followed by performing the subtraction process.

(Fifth Modification)

Figure 23:
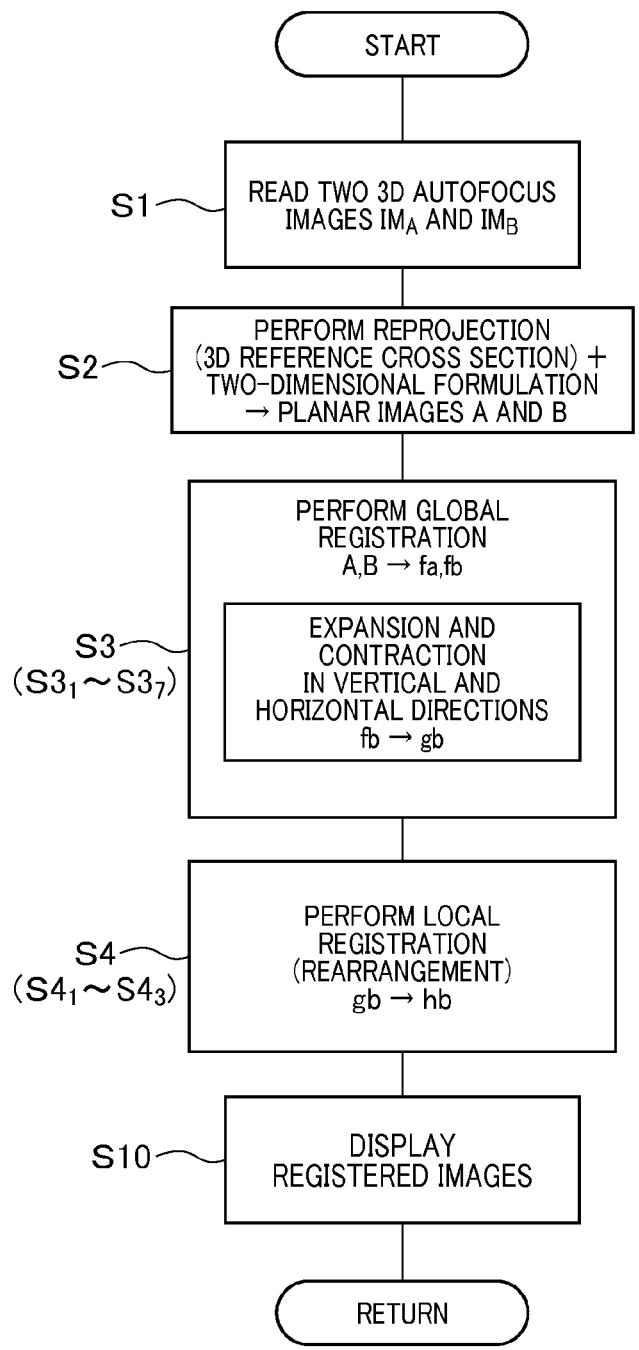
FIG. 23 is a flow diagram schematically illustrating image processing, according to a fifth modification.

As a fifth modification, the foregoing image processor and the image processing method may be modified such that these are performed on the basis of only the registrations. Specifically, taking the foregoing embodiment as an example, in the process shown in FIG. 7 performed by the image processor 35, the registrations up to the steps preceding step S5, i.e. the normalized two planar images fa and gb, may be obtained without performing step S5. The resultantly obtained registered images (either one or both of the two planar images fa and gb) may be displayed on the display 36 or the like (step S10 of FIG. 23). In FIG. 23, steps S1 to S4 are the same as those shown in FIG. 7.

(Sixth Modification)

Figure 24:
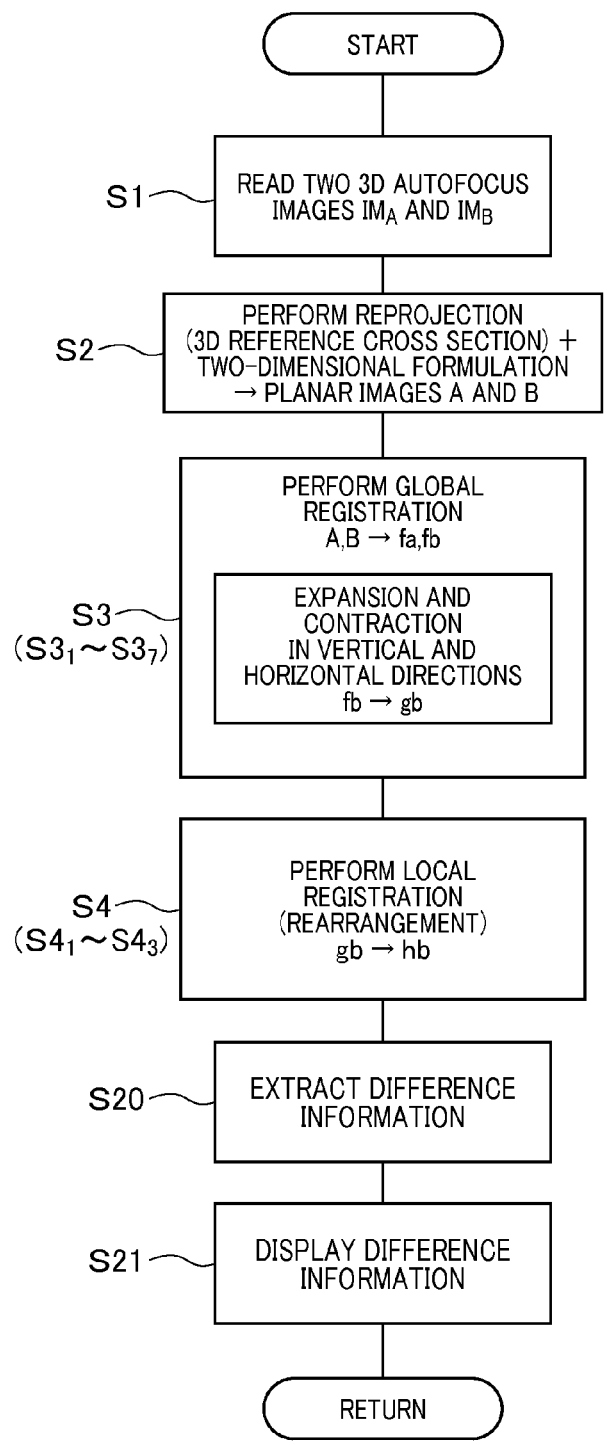
FIG. 24 is a flow diagram schematically illustrating image processing, according to a sixth modification.

FIG. 24 shows a sixth modification. Repeating the foregoing registrations, two or more planar images can be obtained. From the difference information of these planar images, periodontal disease or the like of a tooth row can also be detected. Since the positions of the plurality of planar images are highly accurately normalized through the registrations, the ROIs set at the same positions in these images can show one portion of an object being examined with high accuracy. Accordingly, from between the portions of the plurality of ROIs, difference information can be easily obtained, the difference information including the information on the changes of correlation values and the number of X-ray photons (count), or the information on the changes of beam hardening (step S20 of FIG. 24). For example, the difference information is provided to an image interpreter via the display 36 (step S21 of FIG. 24). In FIG. 24, steps S1 to S4 are the same as those shown in FIG. 7.

Changes in disease conditions are available from the difference information. In other words, the difference information after registrations referred to in the present invention is not limited to include the foregoing subtraction but also include various pieces of information on changes.

(Seventh Modification)

Figure 25:
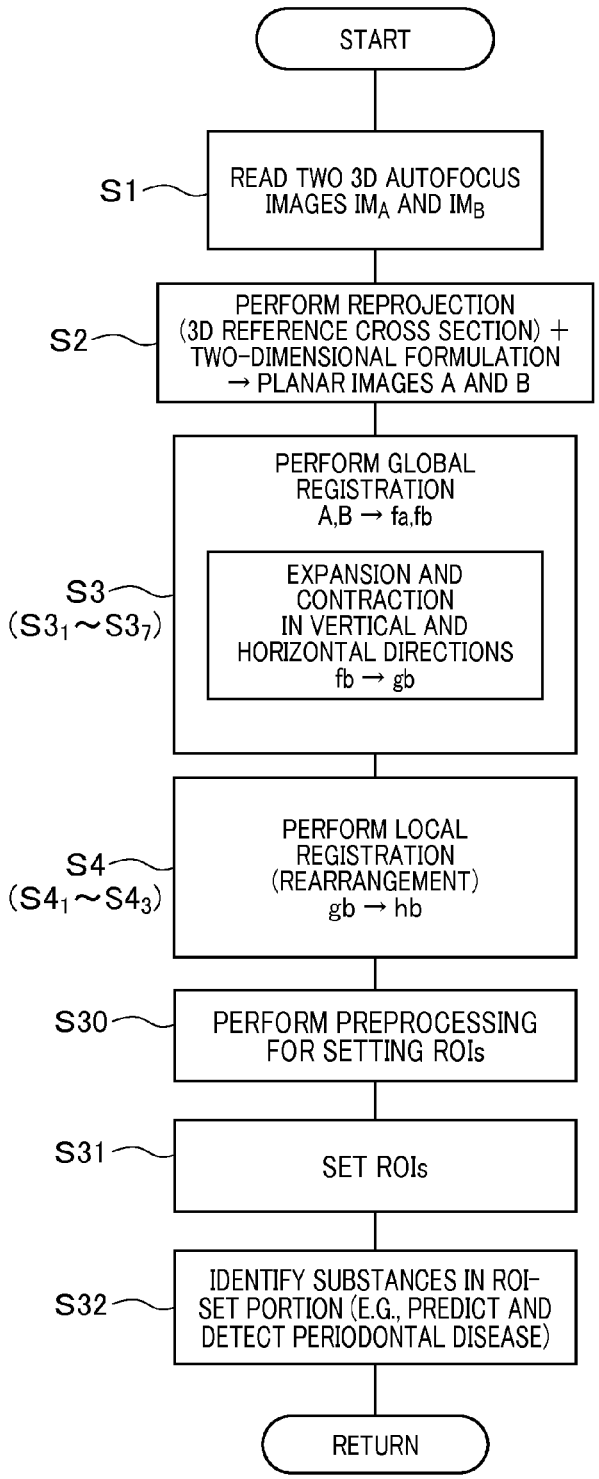
FIG. 25 is a flow diagram schematically illustrating image processing, according to a seventh modification.
Figure 26:
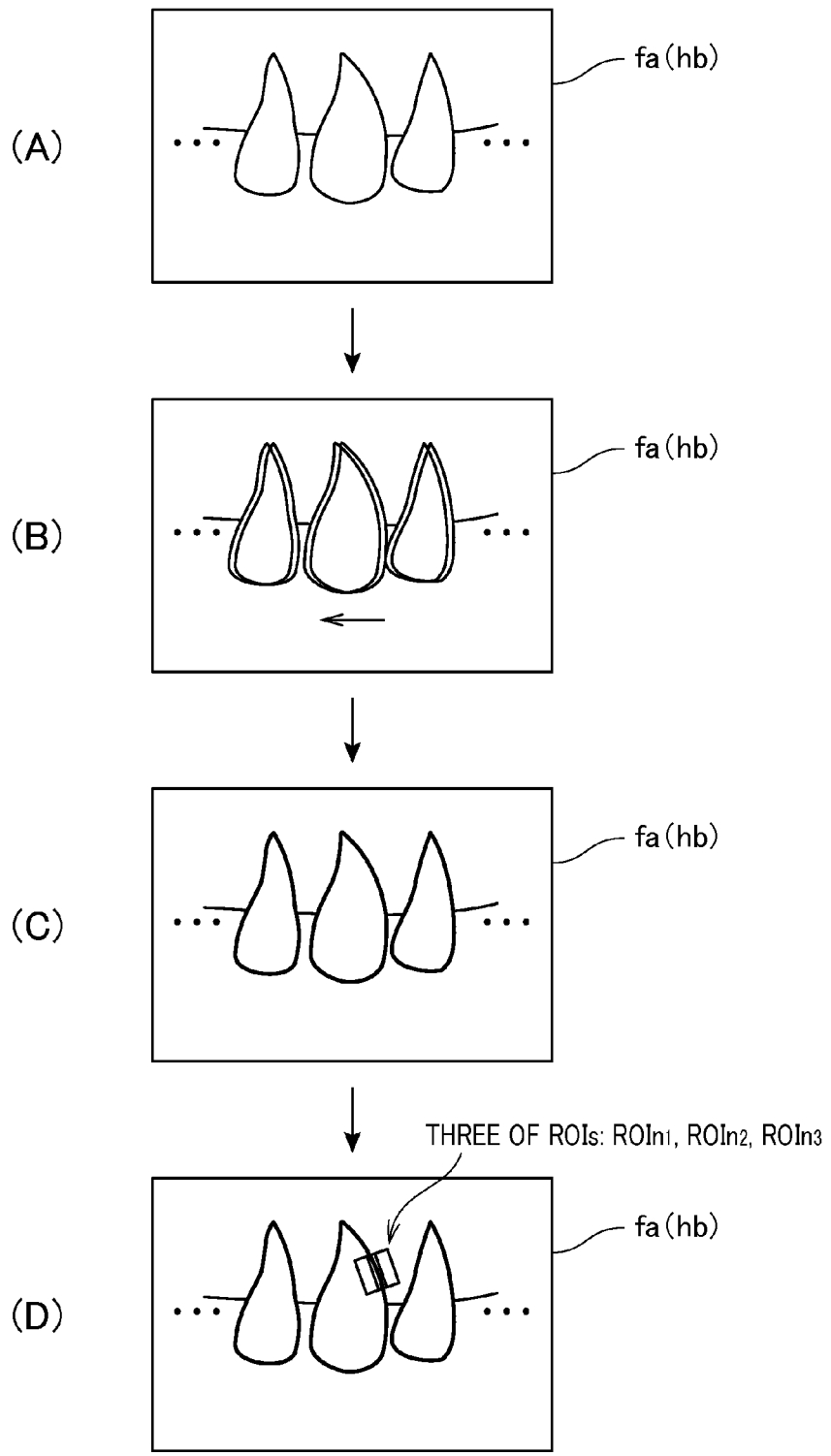
FIG. 26 is a diagram illustrating image processing, according to the seventh modification.

A seventh modification is shown in FIGS. 25 and 26. This modification relates to a method of effectively using the effects of normalization obtained through the registrations of the present invention. Specifically, in the method, the contour of a tooth is more clearly extracted to more correctly set ROIs (regions of interest) in a contoured portion of the tooth.

As typical inflammation caused in a contoured portion of a tooth, periodontal disease (gingivitis, periodontitis) is well known. Considerably progressed periodontal disease can be found via visual observation or conventional panoramic imaging. However, finding out the conditions prior to the occurrence of inflammation, or finding out whether gingivitis is likely to occur, is quite difficult unless the conditions of the internal substances of the alveolar bone or the periodontal membrane are available. In other words, it is necessary to find out the degree of assimilation of the substances that configure the cement, periodontal membrane, gum and alveolar bone of a tooth. To this end, it is required to set ROIs in these respective portions with higher accuracy and identify the local substances in each ROI. Normally, the boundary portion between a tooth and the gum (alveolar bone) is difficult to find in a visual manner in a panoramic image.

In this regard, in the present modification, the boundary portion is more sharpened using the images subjected to the foregoing registrations. Thus, ROIs are ensured to be set with higher accuracy for the prediction and detection of periodontal disease or the like.

The flow diagram shown in FIG. 25 is performed by the image processor 35. In the flow diagram, steps S1 to S4 are the same as those shown in FIG. 7. After the registrations, the image processor 35 performs a preprocessing for setting ROIs in either one of the two planar images fa and hb (see (A) of FIG. 26) (step S30). Specifically, as shown in FIG. 26 by (B), pixels (e.g., three pixels) are displaced to the right or to the left by an amount approximately corresponding to the thickness of the periodontal membrane (e.g., 500 µm) to thereby differentiate the pixel values. Thus, the contour of the tooth is clearly shown (see (C) of FIG. 26)

In this state, the image interpreter sets three rectangular ROIs: ROIn1, ROIn2 and ROIn3, for example, in a contoured portion of the tooth (see step S31: (D) of FIG. 26). In this case, the contour of the tooth has been made clearer. Therefore, the ROIs: ROIn1, ROIn2 and ROIn3 can be set, with high positional accuracy, in portions of the gum (alveolar bone), the periodontal membrane and the cement, respectively.

Then, the substances of the ROI portions are identified (step S32). The identification may be performed using a known method. Alternatively, a scatter diagram may be used, which includes information on the absorption of X-ray beams by substances, and information on the beam hardening of X-ray beams.

According to this modification, higher accuracy is ensured in setting the positions of ROIs for predicting and detecting inflammation such as of periodontal disease at an earlier stage. Therefore, the accuracy of such prediction and detection is also enhanced. In addition, the registrations related to the present invention can be more effectively used.

The foregoing first to seventh modifications may be appropriately combined with each other for implementation.

(Second Embodiment)

Figure 27:
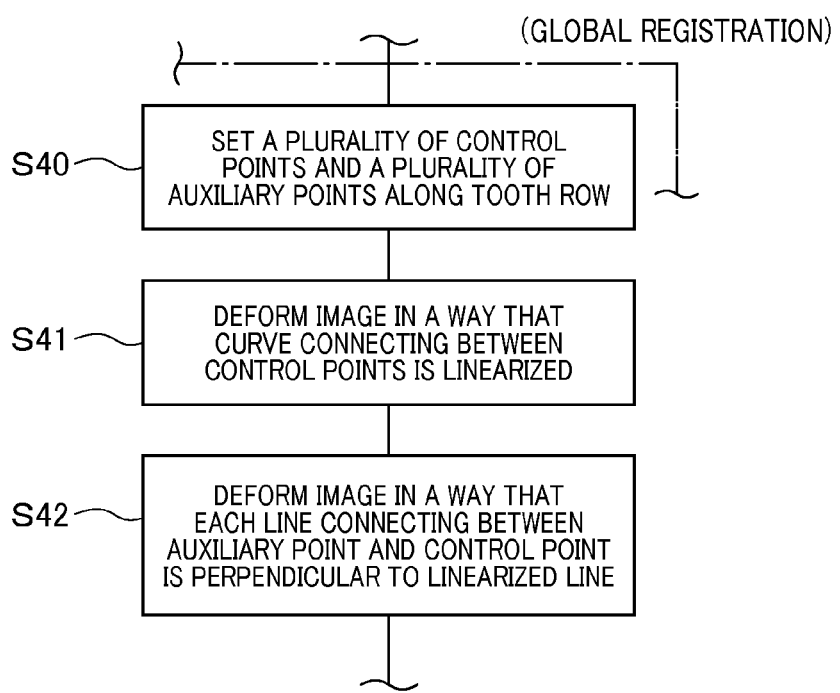
FIG. 27 is a flow diagram illustrating a part of global registration, according to a second embodiment of the present invention.

Referring now to FIGS. 27 and 28, hereinafter is described a second embodiment of the present invention. In the present embodiment, the components identical with or similar to those in the first embodiment are given the same reference numerals for the sake of omitting the explanation.

In image processing related to the second embodiment, the global registration described in the first embodiment is performed with higher accuracy. Accordingly, the global registration related to the present embodiment is characterized in the use of a plurality of auxiliary points in addition to the foregoing plurality of control points $a_0$ to $a_4$.

As shown in FIG. 27, in the global registration, the image processor 35 interactively operates with an operator and sets four auxiliary points $\alpha_1$ to $\alpha_4$ in addition to the five control points $a_0$ to $a_4$ that go along a tooth row (see step S40: (A) of FIG. 28).

Of these points, the five control points $a_0$ to $a_4$ are positioned between the upper and lower tooth rows such that each of the points will be located at a substantially center portion in the width direction of the lower end portion of each specified tooth of the upper tooth row. Of the five control points $a_0$ to $a_4$, the control points $a_0$ and $a_4$ at both ends are set at the lower end centers of the respective right and left third molars each located at the seventh or eighth position from the front. Also, of the auxiliary points $\alpha_1$ to $\alpha_4$, the auxiliary points $\alpha_1$ and $\alpha_4$ at both ends are set in the base portions of the respective third molars.

Of the five control points $a_0$ to $a_4$, the two second control points $a_2$ and $a_3$ from the right and the left are similarly set in respective canine teeth located at the third positions from the front on the right and the left. Of the four auxiliary points $\alpha_1$ to $\alpha_4$, the two auxiliary points $\alpha_2$ and $\alpha_3$ located midway are also similarly set in the respective canine teeth. Of the five control points $a_0$ to $a_4$, the control point $a_2$ in the middle is set at approximately the center of the tooth row.

The reason why the auxiliary points are set is to perform correct registrations of back teeth, taking account that the distortion of the back teeth is normally larger than that of the front teeth, and to thereby enhance the correctness of the entire registrations. Accordingly, the control points $a_0$ and $a_4$ and the auxiliary points $\alpha_1$ and $\alpha_4$ at both ends only have to be set in the backmost molars, and hence may be set in the second molar in the absence of a third molar. In the absence of a second molar, the points may be set in a first molar. When the significance of setting the auxiliary points is concerned, among the four auxiliary points $\alpha_1$ to $\alpha_4$, setting the right-and-left-end auxiliary points $\alpha_1$ and $\alpha_4$ in the respective back teeth is essential. However, depending on the case, the two auxiliary points $\alpha_2$ and $\alpha_3$ located midway, which are set in the respective canine teeth, do not have to be necessarily set. Desirably, an auxiliary point and a control point in a pair are set in the same tooth.

Subsequently, similar to the process in the first embodiment, the image processor 35 approximates a curve drawn by the five control points $a_0$ and $a_4$ on the basis of the Lagrange curve (see (B) of FIG. 28). Then, the image processor 35 displaces the pixels so that the curve is linearized (see (C) of FIG. 28) to thereby deform the image (step S41). Then, as shown by points $\alpha_1'$, $\alpha_2'$, $\alpha_3'$, and $\alpha_4'$, the image processor 35 displaces the pixels such that an approximated straight line Lst will be perpendicular to a straight line Ln1 connecting between the points $a_0$ and $\alpha_1$, a straight line Ln2 connecting between the points $a_1$ and $\alpha_2$, a straight line Ln3 connecting between the points $a_3$ and $\alpha_3$, and a straight line Ln4 connecting between the points $a_4$ and $\alpha_4$ (see (C) of FIG. 28) to thereby deform the image (step S42). In the process of image deformation described above, the amount and the direction of displacement of the points (pixels) other than the control points and the auxiliary points are determined using interpolation on the basis of the amount of displacement accompanying the displacement of the control points and the auxiliary points.

The planar image A (B) resulting from the foregoing process is subjected to the processes similar to those described in the first embodiment, according to the scale factors (steps S3$_3$ to S3$_7$) to generate a subtraction image. At steps S3$_3$ to S3$_6$ in the second embodiment, the target line is the straight line Lst that has already been linearly deformed (see (C) of FIG. 28).

As a matter of course, in the case of making observations focusing on the lower tooth row, points are set in the base portions of the lower teeth in a manner similar to the one described above.

The rest of the configuration and processes is identical with or similar to that of the first embodiment. Accordingly, in addition to the advantageous effects obtained from the first embodiment, this embodiment can provide unique advantageous effects by using the auxiliary points $\alpha_1$ to $\alpha_4$ (or auxiliary points $\alpha_1$ and $\alpha_4$). In other words, compared to the case where only the control points $a_0$ to $a_4$ are used, highly accurate alignment can be conducted, covering from the tip ends of the right and left teeth to the respective base portions. Accordingly, positional accuracy is also enhanced in the registrations and the reliability of the subtraction information is more enhanced.

In the embodiments described above, the target of the processings is a tooth row. However, such a target may be a different portion in a chin portion. Alternatively, such a target may be other portion, such as a joint of an object being examined.

EXPLANATION OF REFERENCES

1 Dental panoramic imaging apparatus functionally and integrally equipped with an image processor
3 Consol
31 X-ray tube
32 Detector
33 Controller
34 First storage
35 Image processor
36 Display
37 Input device
40 ROM

What is claimed is:

1. An image processing apparatus for obtaining difference information between two planar images A and B acquired at two different time points, the planar images being produced based on data indicative of transmission amounts of X-rays transmitted through an object, wherein an X-ray imaging apparatus radiates the X-rays to the object and detects the transmitted X-rays as the data, the image processing apparatus comprising:
first registration means for producing two planar images fa and gb by applying a registration process to overall areas of the two planar images A and B based on curves decided from positions designated on the two planar images A and B respectively, wherein the registration process is performed such that the positions which are set on each of the planar images A and B are aligned along a straight line, both the straight lines corresponding to each other in a horizontal direction, and a scale factor for the registration is changed position by position on the straight lines;
second registration means for searching one of the two planar images, gb, produced by the first registration means, for a match of each of a plurality of local regions composing the other planar image fa, to any of regions of the one planar image gb, and re-projecting images of the matched regions to produce a planar image hb; and
difference calculating means for calculating the difference information between the planar image hb produced by the second registration means and the other planar image fa produced by the first registration means.

2. The image processing apparatus of claim 1, wherein the first registration means comprises
position designating means for designate the plural positions on each of the two planar images A and B interactively with an operator;
curve deciding means for deciding a curve connecting the plural positions designated via the position designating means;
normal-line calculating means for calculating normal lines perpendicular to the curve at plural positions thereon; and
linearizing means for sorting the plural normal lines along a straight line with a scale factor of the plural normal lines changed.

3. The image processing apparatus of claim 1, wherein the first registration means comprises scaling means for obtaining the one planar image fb of which vertical size is adjusted by scaling, wherein, of the two planar images fa and fb, a vertical size of the one planar image fb at each of the horizontal positions thereof is made equal to a vertical size of the other planar image fa at each of the horizontal positions thereof by the scaling.

4. The image processing apparatus of claim 1, wherein the second registration means is provided as means for dividing the other planar image fa by sequentially applying a plurality of types of ROIs, whose sizes are different from each other, to the other planar image fa, and searching, every region divided by the ROIs and every type of the ROIs, the one planar image gb such that the ROIs on the other planar image fa match which local parts of the one planar image gb.

5. The image processing apparatus of claim 1 comprising first displaying means for displaying on a monitor the difference information calculated by difference calculating means.

6. The image processing apparatus of claim 1, comprising
difference information converting means for converging the difference information, which is calculated by the difference information calculating means, to a coordinate system in the two planar images A and B provided before the registration by the first registration means; and
second displaying means for displaying on the monitor the difference information converted by the difference information converging means.

7. The image processing apparatus of claim 6, wherein the second displaying means is provided as means for displaying the difference information superposed on either one or the two of the planar images A and B.

8. The image processing apparatus of claim 6, wherein
the X-ray imaging apparatus comprises
a radiation source which radiates the X-rays;
an X-ray detector which outputs, frame by frame, two-dimensional digital electronic data corresponding to the X-rays in response to incidence of the X-rays thereto;
moving means for moving one selected among a pair of the X-ray source and the X-ray detector, the X-ray detector, or an object relatively to a further one selected therefrom;
data acquiring means for acquiring the data, frame by frame, outputted from the X-ray detector while the moving means move the one selected among a pair of the X-ray source and the X-ray detector, the X-ray detector, or an object relatively to a further one selected therefrom; and
image producing means producing the respective two planar images for each of the two time points based on the data from the same portion being imaged of the same object acquired at the two time points by the data acquiring means, wherein the image producing means produce the two planar images of a desired same tomographic section from an optimally focused three-dimensional image of the portion being imaged of the object, the portion being optimally focused and the three dimensional image representing an actual image and a shape of the portion.

9. The image processing apparatus of claim 1, wherein the X-ray detector is a photon counting type of detector which detects the X-rays as transmission of particles and every range of a preset plurality of divided ranges of energy owned by the X-rays.

10. An image processing method of obtaining difference information between two planar images A and B acquired at two different time points, the planar images being produced based on data indicative of transmission amounts of X-rays transmitted through an object, wherein an X-ray imaging apparatus radiates the X-rays to the object and detects the transmitted X-rays as the data, the image processing method comprising steps of:

producing two planar images fa and gb by applying a registration process to overall areas of the two planar images A and B based on curves decided from positions designated on the two planar images A and B respectively, wherein the registration process is performed such that the positions which are set on each of the planar images A and B are aligned along a straight line, both the straight lines corresponding to each other in a horizontal direction, and a scale factor for the registration is changed position by position on the straight lines;

searching one of the two planar images, gb for a match of each of a plurality of local regions composing the other planar image fa, to any of regions of the one planar image gb, and re-projecting images of the matched regions to produce a planar image hb; and calculating the difference information between the produced planar image hb and the produced other planar image fa.

11. The image processing apparatus of claim 2, wherein the first registration means comprises scaling means for obtaining the one planar image fb of which vertical size is adjusted by scaling, wherein, of the two planar images fa and fb, a vertical size of the one planar image fb at each of the horizontal positions thereof is made equal to a vertical size of the other planar image fa at each of the horizontal positions thereof by the scaling.

12. The image processing apparatus of claim 11, wherein the second registration means is provided as means for dividing the other planar image fa by sequentially applying a plurality of types of ROIs, whose sizes are different from each other, to the other planar image fa, and searching, every region divided by the ROIs and every type of the ROIs, the one planar image gb such that the ROIs on the other planar image fa match which local parts of the one planar image gb.

13. The image processing apparatus of claim 12, comprising first displaying means for displaying on a monitor the difference information calculated by difference calculating means.

14. The image processing apparatus of claim 13, comprising
difference information converting means for converging the difference information, which is calculated by the difference information calculating means, to a coordinate system in the two planar images A and B provided before the registration by the first registration means; and
second displaying means for displaying on the monitor the difference information converted by the difference information converging means.

15. The image processing apparatus of claim 14, wherein the second displaying means is provided as means for displaying the difference information superposed on either one or the two of the planar images A and B.

16. The image processing apparatus of claim 3, wherein the second registration means is provided as means for dividing the other planar image fa by sequentially applying a plurality of types of ROIs, whose sizes are different from each other, to the other planar image fa, and searching, every region divided by the ROIs and every type of the ROIs, the one planar image gb such that the ROIs on the other planar image fa match which local parts of the one planar image gb.

17. The image processing apparatus of claim 16, comprising first displaying means for displaying on a monitor the difference information calculated by difference calculating means.

18. The image processing apparatus of claim 17, comprising
difference information converting means for converging the difference information, which is calculated by the difference information calculating means, to a coordinate system in the two planar images A and B provided before the registration by the first registration means; and
second displaying means for displaying on the monitor the difference information converted by the difference information converging means.

19. The image processing apparatus of claim 18, wherein the second displaying means is provided as means for displaying the difference information superposed on either one or the two of the planar images A and B.

* * * * *